(12) United States Patent
Campi, Jr.

(10) Patent No.: US 11,657,917 B2
(45) Date of Patent: May 23, 2023

(54) COMPUTING DEVICE CONFIGURED WITH USER CHECK-IN FOR MENTAL HEALTH AND WELLNESS

(71) Applicant: Mental Health & Wellness Now Partners, LLC, Wilmington, DE (US)

(72) Inventor: Thomas R. Campi, Jr., Wilmington, DE (US)

(73) Assignee: Mental Health & Wellness Now Partners, LLC, Wilmington, DE (US)

( * ) Notice: Subject to any disclaimer, the term of this patent is extended or adjusted under 35 U.S.C. 154(b) by 0 days.

(21) Appl. No.: 17/809,104

(22) Filed: Jun. 27, 2022

(65) Prior Publication Data

US 2022/0415500 A1  Dec. 29, 2022

Related U.S. Application Data

(60) Provisional application No. 63/215,027, filed on Jun. 25, 2021.

(51) Int. Cl.
| | | |
|---|---|---|
| *G16H 40/67* | (2018.01) | |
| *G16H 10/60* | (2018.01) | |
| *G16H 20/70* | (2018.01) | |
| *G16H 40/20* | (2018.01) | |
| *G16H 10/20* | (2018.01) | |

(52) U.S. Cl.
CPC .............. *G16H 40/67* (2018.01); *G16H 10/20* (2018.01); *G16H 10/60* (2018.01); *G16H 20/70* (2018.01); *G16H 40/20* (2018.01)

(58) Field of Classification Search
CPC ........ G16H 40/67; G16H 40/20; G16H 10/60; G16H 10/20; G16H 20/70
See application file for complete search history.

(56) References Cited

U.S. PATENT DOCUMENTS

| | | |
|---|---|---|
| 2011/0087076 A1* | 4/2011 | Brynelsen et al. |
| 2012/0215560 A1* | 8/2012 | Ofek et al. |
| 2014/0257931 A1* | 9/2014 | Rinzler |
| 2016/0283664 A1* | 9/2016 | Tubman et al. |
| 2017/0011188 A1* | 1/2017 | Arshad et al. |
| 2017/0046496 A1* | 2/2017 | Johnstone et al. |
| 2017/0300643 A1* | 10/2017 | Bezark et al. |
| 2018/0101659 A1* | 4/2018 | Ninan et al. |
| 2021/0110354 A1* | 4/2021 | Chennupati et al. |

* cited by examiner

*Primary Examiner* — Michael Tomaszewski
*Assistant Examiner* — William T. Monticello
(74) *Attorney, Agent, or Firm* — Tatonetti IP

(57) ABSTRACT

Implemented is a check-in application instantiated on a user's local computing device, adapted to receive user updates on their current mental health status. The check-in application invites users to check in as frequently as they'd like and provides a calendar with push notifications to serve as reminders for users to check in. Each check-in response is assessed to determine a mental health severity level for a given user, typically broken down into low, medium, and high severity levels. Each severity level is associated with a set of automated procedures that the check-in application initiates based on the detected severity level. An incentive-based award system is also utilized within the check-in application to encourage users to periodically and consistently use the application.

17 Claims, 29 Drawing Sheets

(Enlarged for clarity in exposition)

FIG 24

Mental Health & Wellness Now ™ Telehealth  05/17/2022 1:30 PM

Potential Earnings: +$130,055

Weekly Appointments

| | Care Note Scheduled? 2410 | Must Follow Patient? 2415 | Therapy 2420 +$130,055 175 out of 690 enrolled 690 hrs wk / 17.2 Team Show rate: 100% | Meds 2425 +$35,625 200 out of 750 enrolled 172.5 hrs wk / 4.31 Team Show rate: 100% | Coaching 2430 +$25,000 50 out of 500 enrolled 345 hrs wk / 8.63 Team Show rate: 100% |
|---|---|---|---|---|---|
| Last Check-in 2405 20 days avg. | | | | | |
| 46 days | Yes | Yes | Therapy 90834 $141.35 45 min 05/15/2022 last | Eval & Manage 99213 $47.50 15 min 05/15/2022 last | Coaching out-of-pocket $50.00 30 min 05/22/2022 target |
| 1 days | Yes | Yes | Therapy-2x wk 90834 $141.35 45 min 05/15/2022 last 05/22/2022 target | E & M - 2x wk 90834 $47.50 45 min 05/15/2022 last 05/22/2022 target | Coaching out-of-pocket $50.00 30 min 05/22/2022 last |
| 2 days | No | No | Not enrolled | Eval & Manage 99213 $47.50 15 min 05/22/2022 target | Coaching out-of-pocket $50.00 30 min 05/22/2022 target |

FIG 25

[Patient Name]

Back

Search Names 🔍

Name
(XXX) XXX-XXX
Dr. XXXXXX

| | Now Evaluations | Now Follow-ups | Daily Follow-ups | Weekly Follow-ups | Therapy Appointments | Meds Appointments | Coaching Appointments | Care note Scheduled? | Must Follow Patient? |
|---|---|---|---|---|---|---|---|---|---|
| | Auto | On | On | On | On | On | Off | Yes | Yes |

05/26/2022 10:00 AM

☐ "Not safe(personal reply)"
Follow-up ○ Now & Anytime
○ Daily & Anytime
○ Weekly & Anytime This Month   3 Months   This year Clinical Note submitted in EMR, for all Dr. Team staff engagement:

( Note submitted )  ( on date/time )  ( signed Dr. Team Staff name )

Mood

5/17 5/18 5/19 5/20 5/22 5/24 5/25 5/26

| | Totals |
|---|---|
| ☐ "I'm good" | 0 |
| ☐ "Safe" (personal reply)" | 0 |
| ☐ "I'm meh" | 1 |
| ☐ "I'm struggling but feel safe" | 4 |
| ☐ "Not safe (personal reply)" | 1 |
| ☐ "I could use a Dr. Team Check-in" | 0 |
| ☐ "I'm in a dark place" | 2 |

If applicable, follow-up contact issues:

( No response on chat )( No reply to call )( No reply text! )( Email request sent )( Other )( on date/time )( signed Dr, Team Staff name )

Status Changes:

Must Follow Patient? Yes on 5/26/2022 11:30 AM signed by: Dr. Team Staff Member Name
Medium severity Triage 4x in 1 month -> High Severity on 5/25/2022 10:00 AM signed by: Automatic Execution
Now Follow-up Off. Yes rationale: patient reported safe on 5/18/2022 11:30 AM signed by: Dr. Team Staff Member
Care Note Scheduled? Yes on 5/17/2022 11:30 AM signed by: Dr. Team Staff Member Name
Coaching Enrollment Off. Yes rationale: starting therapy & meds first on 5/16/2022 11:30 AM signed by: Dr Team
New Patient? No on 5/16/2022 10:00 AM signed by: Dr. Team Staff Member Name

[Additional Patient Information]
(FIG 26)

FIG 26

[Additional Patient Information from FIG 25]

Check-in; "Not safe...I'm scared"

Check-in; Date 5/26/2022
Check-in; Time 10:00 AM
After Hours: No
Count Down Timer: Yes
Count Down Timer: 15 out of 60 seconds
Follow-ups: Now & Anytime, Daily & Anytime, Weekly & Anytime
E-mail: patient@gmail.com
First Name: PatientFirstName
Last Name: PatientLastName
Gender: Female
Pronouns: she/her Mental Health: Not good, need Dr. Team... "depressed"
Wellness: Not OK
Sleep & Appetite: Not good, need Dr. Team..."poor"
Side Effects: I'm OK.
Hearing Voices / Seeing Visions: I'm Ok.
Suicidal / Homicidal Thoughts: Not good, need Dr. Team..."Suicidal"

Mobile Phone: XXX-XXX-XXX
Age: XX
Where now: home
Home address: XXX Main Street, Anytown, Anystate, Anyzip
Emergency Contact Name: PatientMomFirstName PatientMomLastName
Emergency Contact Telephone: XXX-XXX-XXX
Emergency Contact Relationship: Mom Next Scheduled Appointment: 05/31/2022 1:00 PM

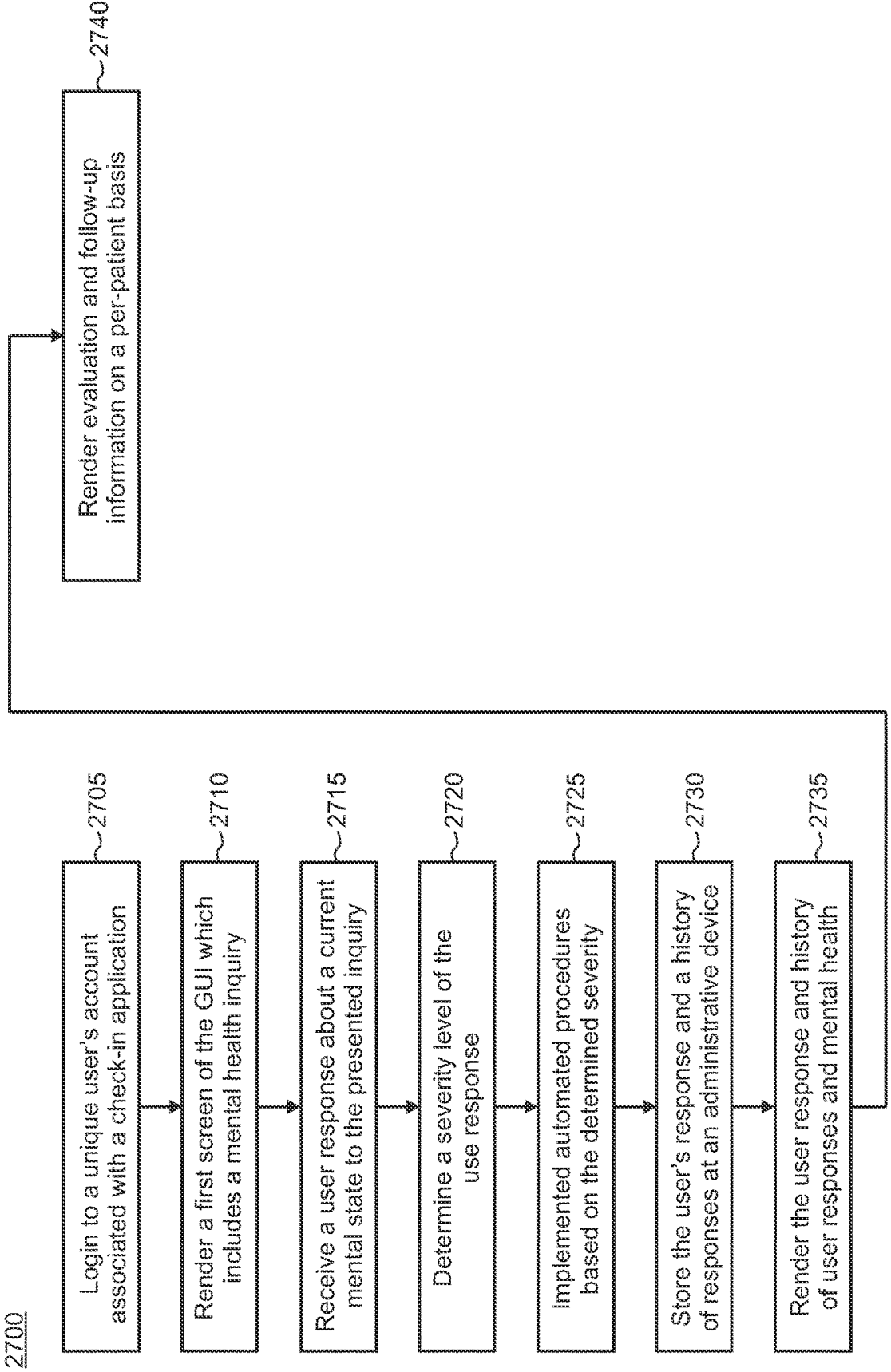

COMPUTING DEVICE CONFIGURED WITH USER CHECK-IN FOR MENTAL HEALTH AND WELLNESS

CROSS-REFERENCES TO RELATED APPLICATIONS

This Non-Provisional Utility Patent application claims the benefit of and priority to U.S. Provisional Application Ser. No. 63/215,027, filed Jun. 25, 2021, entitled "Automated Triage, Crisis Response, Determination, Scheduling, Scheduling User-Interface Generation, and Notification of Care, Self-Care, Activities, and Other Detriments of Mental Health, Wellness, Self-Efficacy, and Resilience Based on Engagement with User Interface Check-In Automation Tools," the entire contents of which is hereby incorporated herein by reference.

BACKGROUND

Current approaches to preventing suicide are ineffective as the suicide rate continues to increase. According to some data, the suicide rate for both genders is increasing—12.5 suicides per 100,000 population in 2019. In females, the suicide rate of all ages is both increasing and too high, and notably, the rates are increasing highest for the early teens and the youth. Social media is at least one contributing factor, as data shows an alarming association between screen time misuse and self-harm. Depression is prevalent in female teens, as high as 30 percent. Put simply, current systems in place to prevent suicide and depression are failing the youth and young teens.

Depression alone is reported to cost $1 trillion a year globally in lost productivity. Notably, a recent WHO (World Health Organization)-led study estimated that for every $1 (USD) into proper treatment for common mental disorders, there is a return of $4 in improved health and productivity. Disability income and affordable housing brought on by mental illnesses can also be preventable, which would save substantial resources.

A prevention-based approach is lacking for a coordinated public health effort—involving public and private applied strategies, outreach, and monitoring for innovative system change. Current government 'soft-dollars' are already allocated to large public entities, state-influenced, and non-profit hospitals that support and depend on existing infrastructure and annual funding. Grants to private industry can facilitate enterprise innovation self-sustainment—a coordinated approach for mental health and wellness from all public and private funding sources.

SUMMARY

Implemented is a check-in application instantiated on a user's local computing device, adapted to receive user updates on their current mental health status. The check-in application invites users to check in as frequently as they'd like and provides a calendar with push notifications to serve as reminders for users to check in. Each check-in is assessed to determine a mental health severity level for a given user, typically broken down into low, medium, and high severity levels. Each severity level is associated with a set of automated procedures that the check-in application initiates based on the detected severity level.

Low and medium severity levels may still enable a user to reach out for counseling but otherwise may provide the user with mental health reading and video materials to enable the user to continue practicing good mental health. Low and medium severity levels may also provide users with an additional inquiry about the user's mental health to glean some additional information about the user to, for example, verify that the user is not at high risk of harming themselves or others. High severity mental levels may initiate an automated process by which a medical provider is invited for an immediate virtual conversation with the user. If no medical provider is available, the user is contacted by multiple medical help intervention sources, such as 911, suicide prevention hotlines, etc.

The check-in application is also configured to incentivize users to periodically and routinely check in at the check-in application, such as financial incentives. The check-in application provides a dashboard section that allows users to view their accrued financial benefits.

The streamlined presentation of the check-in application and its dedicated invitation to receive user check-in responses provides a unique method by which those with mental health issues can be easily identified and cared for. For example, user mental health responses are typically performed in a straightforward "click" format by which users can tap how they feel on their touchscreen smartphone. Thus, once the user logs into their account, a single tap on a pre-set option that describes how the users feel can put them in immediate contact with a medical provider or a suicide hotline. Notably, the easy-to-use and streamlined user experience train the user to use the check-in application—with an incentive-based system—so the user is already comfortable with and trained to use the check-in application if they need help. Such a patterned user interface and automated procedure results in an easy and resource-savings scenario and puts users in direct communication with doctors regularly and consistently.

This Summary is provided to introduce a selection of concepts in a simplified form that is further described below in the Detailed Description. This Summary is not intended to identify key features or essential features of the claimed subject matter, nor is it intended to be used as an aid in determining the scope of the claimed subject matter. Furthermore, the claimed subject matter is not limited to implementations that solve any or all disadvantages noted in any part of this disclosure. It will be appreciated that the above-described subject matter may be implemented as a computer-controlled apparatus, a computer process, a computing system, or as an article of manufacture such as one or more computer-readable storage media. These and various other features will be apparent from reading the following Detailed Description and reviewing the associated drawings.

BRIEF DESCRIPTION OF THE DRAWINGS

FIG. 10 shows an illustrative user interface in which the user is presented with a closing screen after their check-in;

FIG. 13 shows an illustrative user interface in which the user is presented with a closing screen after their check-in;

FIG. 17 shows an illustrative user interface in which the check-in application is configured to provide scheduled notifications to the user to check in;

FIGS. 23 and 24 show illustrative user interfaces of the administrator's backend display;

FIGS. 25 and 26 show illustrative user interfaces of the administrator's backend display;

FIG. 27 shows an illustrative process that may be implemented by a user's computing device, remote server, periphery computing device, or a combination thereof;

Like reference numerals indicate like elements in the drawings. Elements are not drawn to scale unless otherwise indicated.

DETAILED DESCRIPTION

Figure 1:
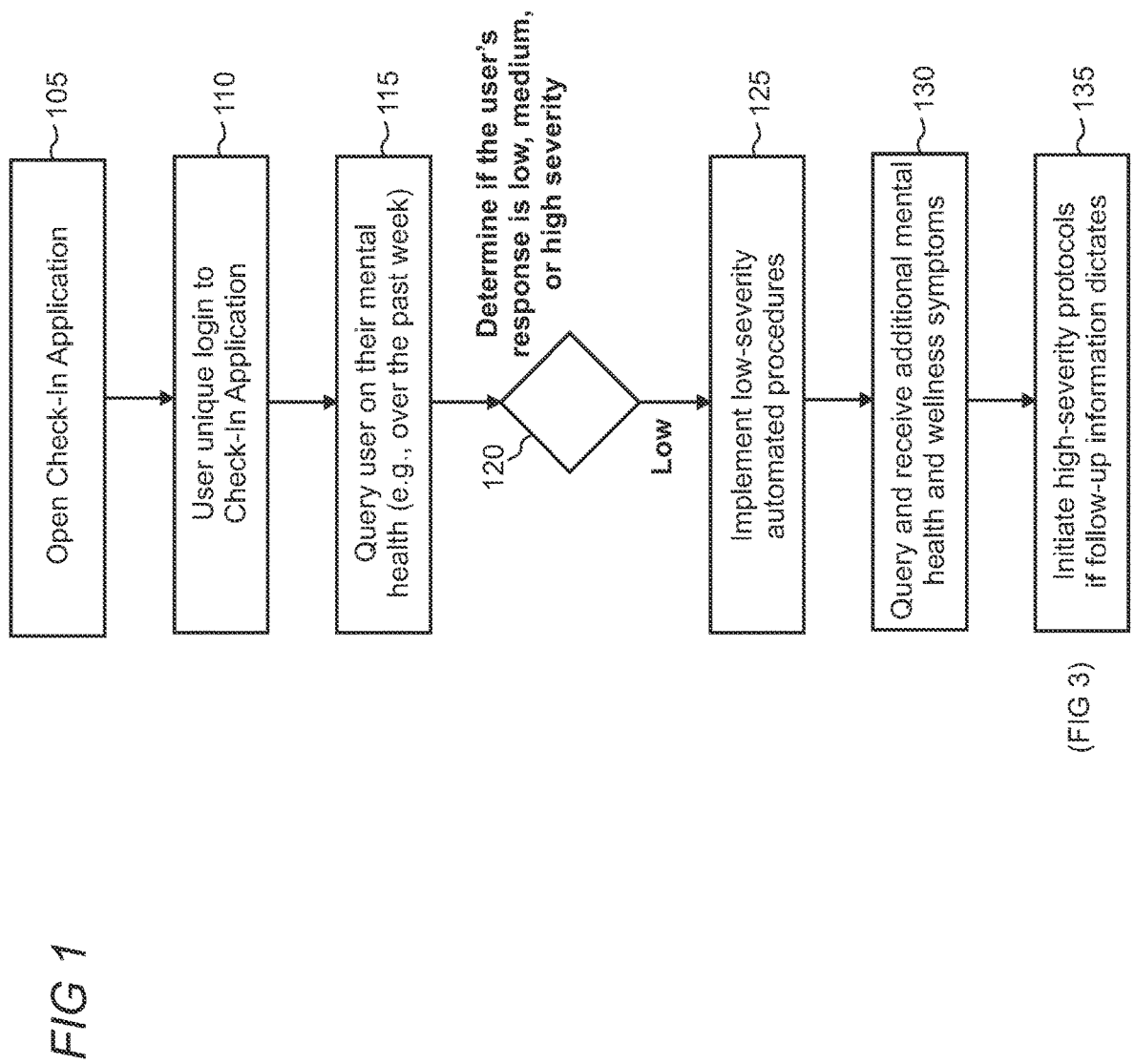
FIG. 1 shows an illustrative flowchart of a low-severity response by the check-in application.
Figure 2:
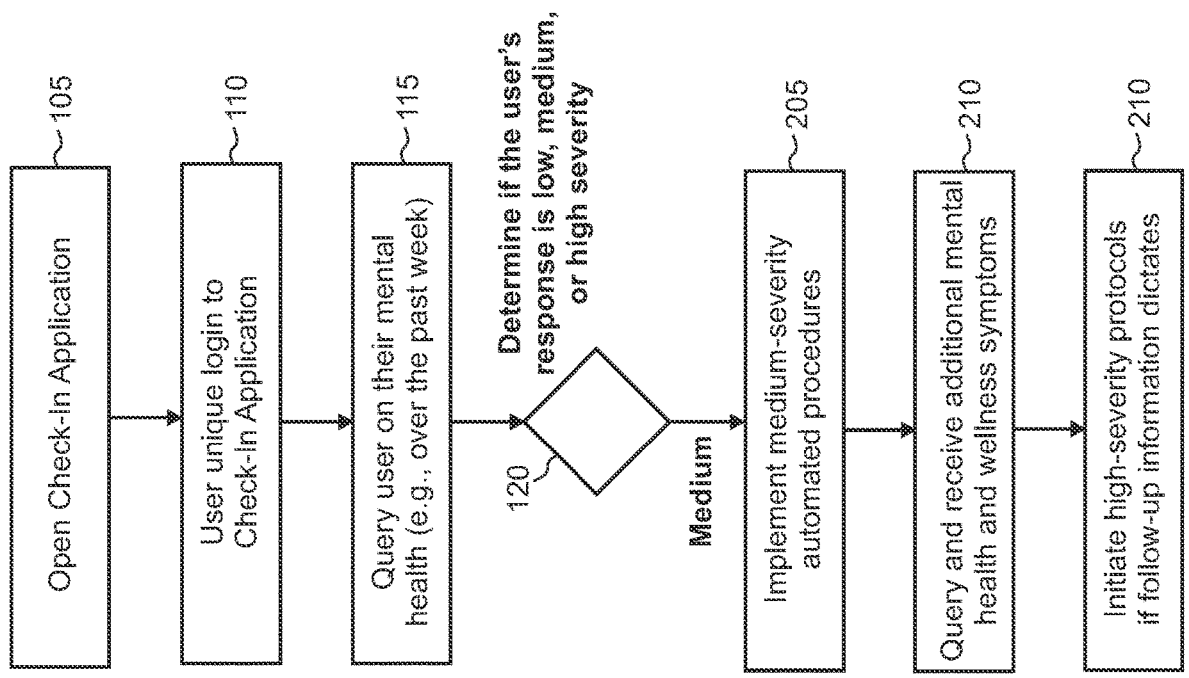
FIG. 2 shows an illustrative flowchart of a medium-severity response by the check-in application.
Figure 3:
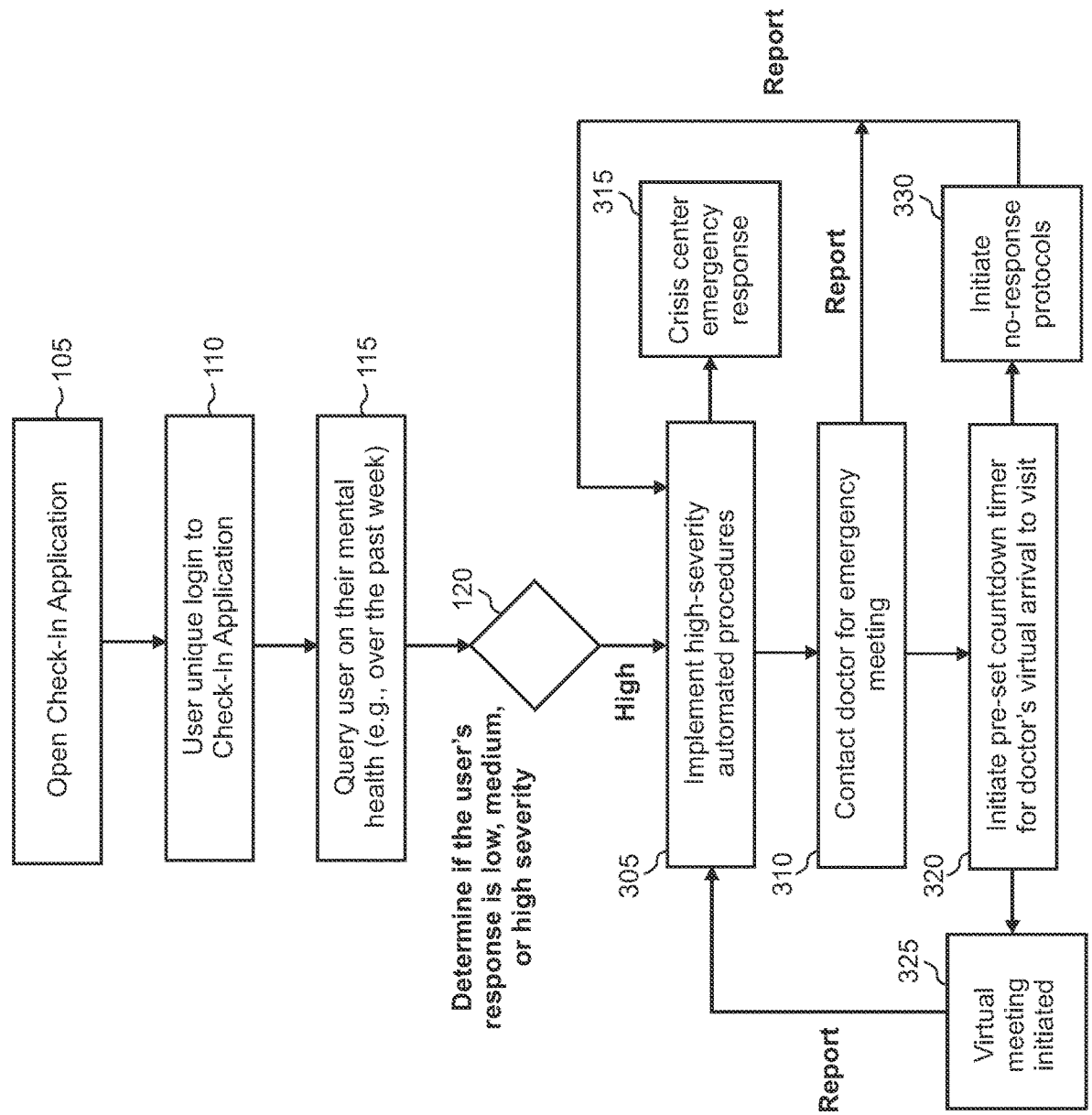
FIG. 3 shows an illustrative flowchart of a high-severity response by the check-in application.

FIGS. 1-3 show illustrative processes that a check-in application instantiated on a user's computing device may follow to provide a mental safety net for users. The check-in application may be instantiated on a user's mobile device, such as a smartphone, tablet computer, laptop, or other computing devices, including a desktop computer. The check-in application may be locally installed, remotely installed on a remote server, accessed via a local application, or a combination of both. Thus, the features discussed herein may leverage locally or remotely executing code.

In step 105, the check-in application is opened on the user's computing device, such as responsive to user selection of the application. For example, the user may click on a graphical user interface (GUI) icon presented on the user's screen or opened via some alternative command or input, such as a voice command. In some implementations, the check-in application may be a plug-in that is part of and selectable via another application.

In step 110, the user logs into the check-in application. The user may enter a username (e.g., unique name, e-mail address, alphanumeric characters, etc.) that identifies the specific user and a password to access the account associated with the user name. Other authentication techniques may also be utilized, such as biometrics (e.g., facial recognition, fingerprint matching, iris scan, etc.), numerical PIN (personal identification number) codes, etc.

In step 115, the check-in application queries the user on their mental health over a period of time (e.g., over the past week, day, few days, month, etc.). The user may be presented with a series of pre-set options to select, type in their own unique response, or a hybrid approach, as discussed in greater detail below.

In step 120, the check-in application—either using locally- or remotely-accessible code, determines if the user's response indicates low, medium, or high severity in order to present a suitable response. The check-in application's subsequent user interfaces and presentations may increase in extremity depending on the user's determined severity.

In step 120, in FIG. 1, the check-in application determines that the user's severity level is low based on their response. In step 125, the check-in application employs low-severity automated procedures. This may include, for example, displaying a final screen thanking the user for their input, providing the user with encouragement, and reminding the user that they can check in any day and time. Additionally, the user may be presented with the option to revert to the check-in screen if they, in fact, do not feel well. The user may be presented with mental health and wellness resources for education and symptoms strengthening, including links to websites, proprietary or third-party documents, pamphlets, in-app information, etc.

In addition, periodic check-ins on the application may be scheduled, such as weekly check-ins at 10:00 a.m. on Fridays. Given the user is in a low-severity state, less frequent check-ins may be scheduled. The check-in application may interoperate with a calendar application, such as Google® Calendar, Outlook®, Apple® Calendar, etc., in which links to the check-in application or URL (uniform resource locator) accessible via a web browser application so that the user can always access the check-in application regardless of their device.

In step 130, responsive to the low severity determination, the check-in application queries the user and receives additional mental health and wellness symptoms. For example, such a follow-up query may provide greater insight into the user's mental health since the application has established the user is in a low-severity state. This may be an optional step depending on the specific implementation. In step 135, if the user's additional input symptoms indicate a high-severity scenario, then the check-in application may initiate high-severity protocols (FIG. 3).

The process in FIG. 2 follows similar procedures as FIG. 1 but diverges based on the determination that the user's response indicates medium severity. In step 205, the check-in application implements medium severity automated procedures. Medium severity, in some embodiments, may signify that the user is unhappy but feels safe (i.e., they will not hurt themselves or others). The medium-severity response can include determining a schedule for a check-in notification system, such as daily 10:00 a.m. reminders to utilize the check-in application and input their symptoms. Other frequencies may also be possible, such as weekly automation (e.g., every Friday at 1:00 p.m.), bi-daily, etc.

The medium-severity response may further include, for example, displaying a final screen thanking the user for their input, providing the user with encouragement, and reminding the user that they can check in any day and time. Additionally, the user may be presented with the option to revert to the check-in screen if they, in fact, do not feel well. The user may be presented with mental health and wellness resources for education and symptoms strengthening as well, which may include links to websites, proprietary or third-party documents, pamphlets, in-app information, etc.

In step 210, the check-in application optionally queries the user and receives additional mental health and wellness symptoms. This may further investigate the user's mental health to identify potential problems. In step 215, if the follow-up inquiry indicates that the user may be better characterized as a high-severity case, then the check-in application may initiate high-severity protocols (FIG. 3).

The process in FIG. 3 follows similar procedures as FIGS. 1 and 2 but diverges based on the determination that the user's response indicates high severity. In step 305, the check-in application implements high severity automated procedures responsive to determining the user's response is high severity at step 120. In step 310, the check-in application may send a message to a medical provider staff for a psychiatric evaluation. Any reference to a "medical provider" or "Dr. Team" herein does not solely represent a medical professional, but any person or employee that is part of the medical provider or Dr. Team staff, including medical doctors, physician assistants, nurses, non-medical staff and employees, and any other person that is sufficiently trained or trusted to intervene or partake in the situation, such as a patient video call, whether temporary or otherwise. The message may be a text message, e-mail, automated or personal phone call from an employee, push notification via the check-in application, etc. Step 310 may be one of the high-severity automated procedures, but other automated tasks may also be part of the high-severity procedures.

In step 320, and while the doctor is being contacted, the check-in application may present the user with a countdown timer that indicates an expected wait time until a member of the medical provider staff (e.g., doctor, psychiatrist, psychologist, nurse, physicians assistant, etc.) is available for a meeting, such as a virtual video conversation, telephone conversation, text or e-mail conversation, or a combination thereof.

In step 315, a crisis center emergency response may be implemented, which may include a medical provider being immediately available for messaging or conversation and thereby bypassing the timer in step 320. The conversation may be engaged over a virtual chat inside the application or connecting to another application installed on the patient's and doctor's computing device.

In step 325, the virtual meeting may be initiated when the medical provider is available for the conversation. In step 330, however, the check-in application may initiate no-response protocols, such as when the dr. team staff is busy. This may include any one or more of an immediate referral to emergency care 911, hospital emergency room, suicide prevention lifeline, emotional support chat with another available individual, or providing the telephone number to the dr. team's staff. The check-in application may initiate a conversation with a remote provider, such as 911 or a hotline, or may provide the user with the contact information.

In steps 310, 325, and 330, the check-in application may report the results to a remote server for storage. Medical providers and system administrators may use this data to assess the check-in application's results and statuses. Such results may be presented on a system administrator's or medical provider's computing device, which has access to the remote server's backend data.

Figure 4:
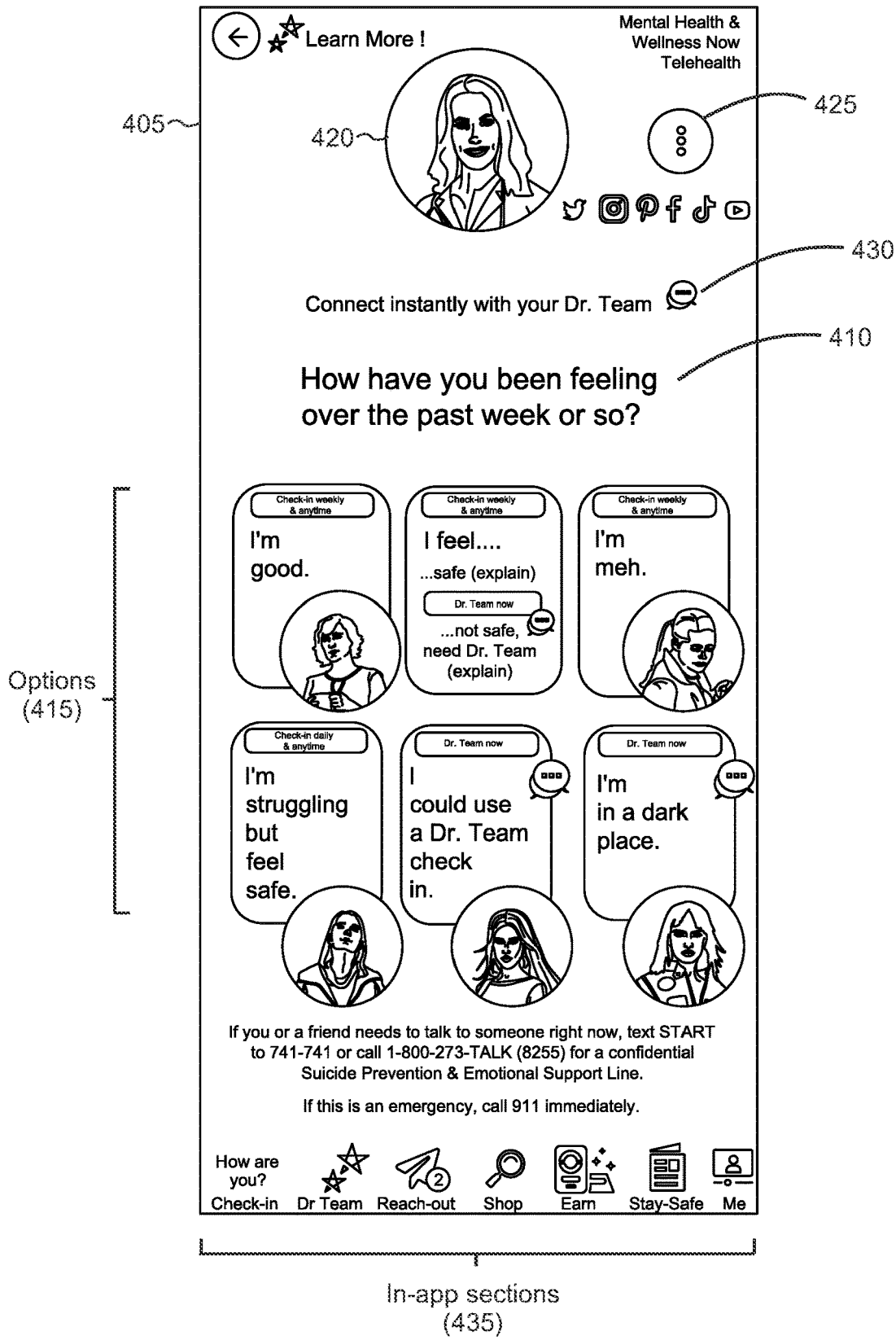
FIG. 4 shows an illustrative user interface in which the check-in application queries the user on their mental health.

FIGS. 4-18B show illustrative user interfaces (UIs) on a user's local computing device, such as a smartphone, that effectuate the check-in application's features, such as that described regarding the processes in FIGS. 1-3. FIG. 4 shows an illustrative user interface on computing device 405 in which the user is presented with a query about how they have been feeling over the past week 410. The user is presented with pre-set options 415 that the user may select with a touchscreen display, pointing device (e.g., mouse), voice command, etc. The presented options help determine the user's mental state, such as if they are in a low, medium, or high severity state.

Some options may be entirely pre-set, and others may provide a hybrid approach. For example, the user can select "I'm good," "I'm meh," "I'm struggling but feel safe," "I could use a Dr. Team check-in," or "I'm in a dark place." Alternatively, the option "I feel . . . " is an open-ended question to which the user can type a response. The system may be configured to designate symptoms into labels such as "safe" or "not safe" categories, and/or identify specific words or phrases as problematic, such as "death," "suicide," "terrific," "happy," "suck," etc. Suck words may be configured into the system's code for identification and associating responses. The system may alternatively present the user with a series of adjectives for the user to describe their wellbeing so that the user can "fill in the blank." If the check-in application is ever unclear as to the user's dynamic response, then a responsive action may be performed, such as flagging an employee of the company, such as a dr. team staff member, for review, sending the message to a medical provider for review, and asking the user to enter a different response, etc.

The UI in FIG. 4 includes a picture or avatar 420 of the user associated with their account. Icon 425 may provide the user with a selection of settings for the application responsive to being touched, such as changing their profile photo or avatar 420, changing their password, contacting an emergency hotline, etc. The user may select text 430 to connect to a healthcare professional automatically. At the bottom of the check-in application's UI are a series of in-app sections 435 that the user may select to explore different features provided by the application. This includes, from left to right, the check-in function currently displayed in FIG. 4, the ability to see the Dr. team, reach out to other professionals, shop within the application, earn rewards or cash screen, stay-safe tab, which may provide the user with mental health information, and a "Me" tab that may be a unique user profile.

Figure 5:
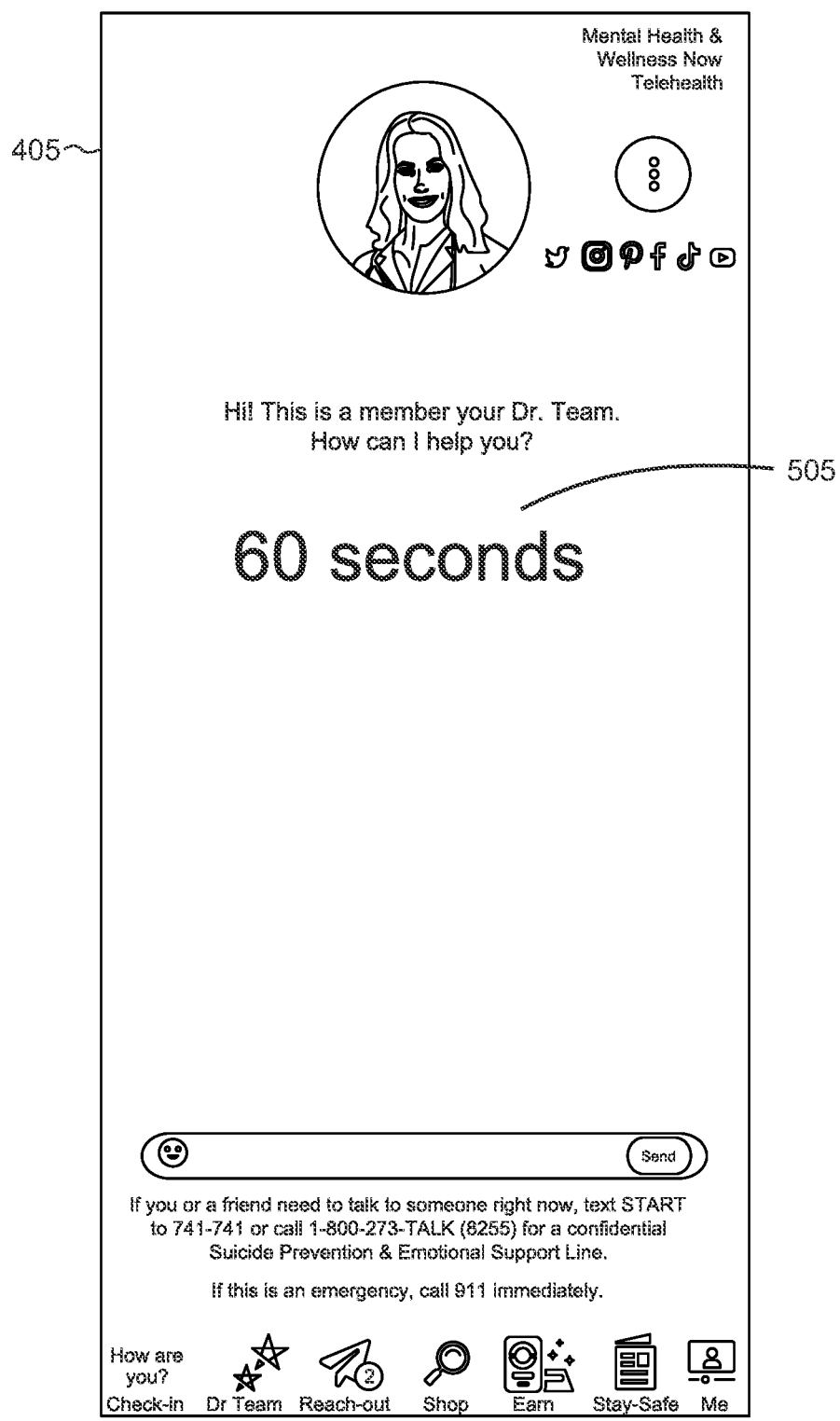
FIG. 5 shows an illustrative user interface in which the countdown timer is presented to the user.

FIG. 5 shows an illustrative UI in which the check-in application determined that the user's check-in response at FIG. 4 indicates a high severity situation. The UI presents the user with a countdown timer 505 of 60 seconds, but other times may also be presented, such as 15 seconds, 30 seconds, two minutes, etc. The countdown time used may vary based on, for example, the gravity of the user's response to the check-in on FIG. 4—less severe responses may present a two-minute standard timer, and more severe responses (e.g., I have a gun in my hand) may result in a shortened 15-second timer.

Figure 6:
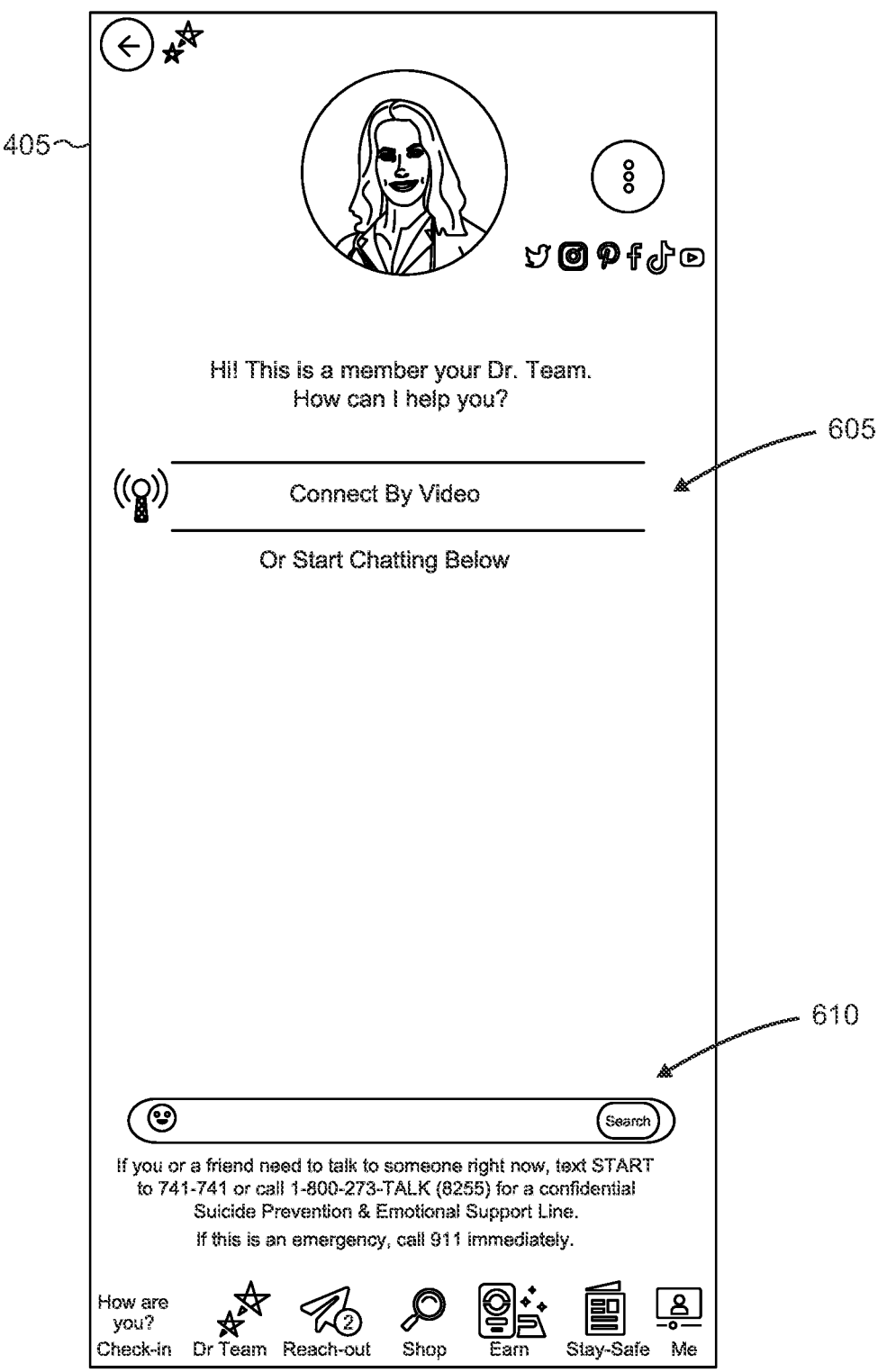
FIG. 6 shows an illustrative user interface in which the user can select communicating with a doctor.

Simultaneously, before or immediately after presenting the UI in FIG. 5, the check-in application may implement the high severity automated procedures. FIG. 6 shows an illustrative UI in which the user is presented with communication options 605 to initiate a virtually immediate conversation with a medical provider. The communication options can include video chat or text chat. The video chat may utilize a module associated with the check-in application to create an in-app video meeting. Alternatively, the video chat may interoperate with a third-party application installed on the user's device or using a web browser. The texting option may utilize a textbox 610 within the check-in application and on the same screen as the presented communication options 605. Any conversation may propagate above the textbox and below the communication options or may open up a follow-on screen dedicated to the texting. In other embodiments, a third-party application instantiated on the user's device or within a web browser may enable the user to chat. When third-party communication applications or a web browser are used, the check-in application may create the communication session dedicated to the logged-in user and the medical provider, when ready, to maintain privacy.

Figure 7:
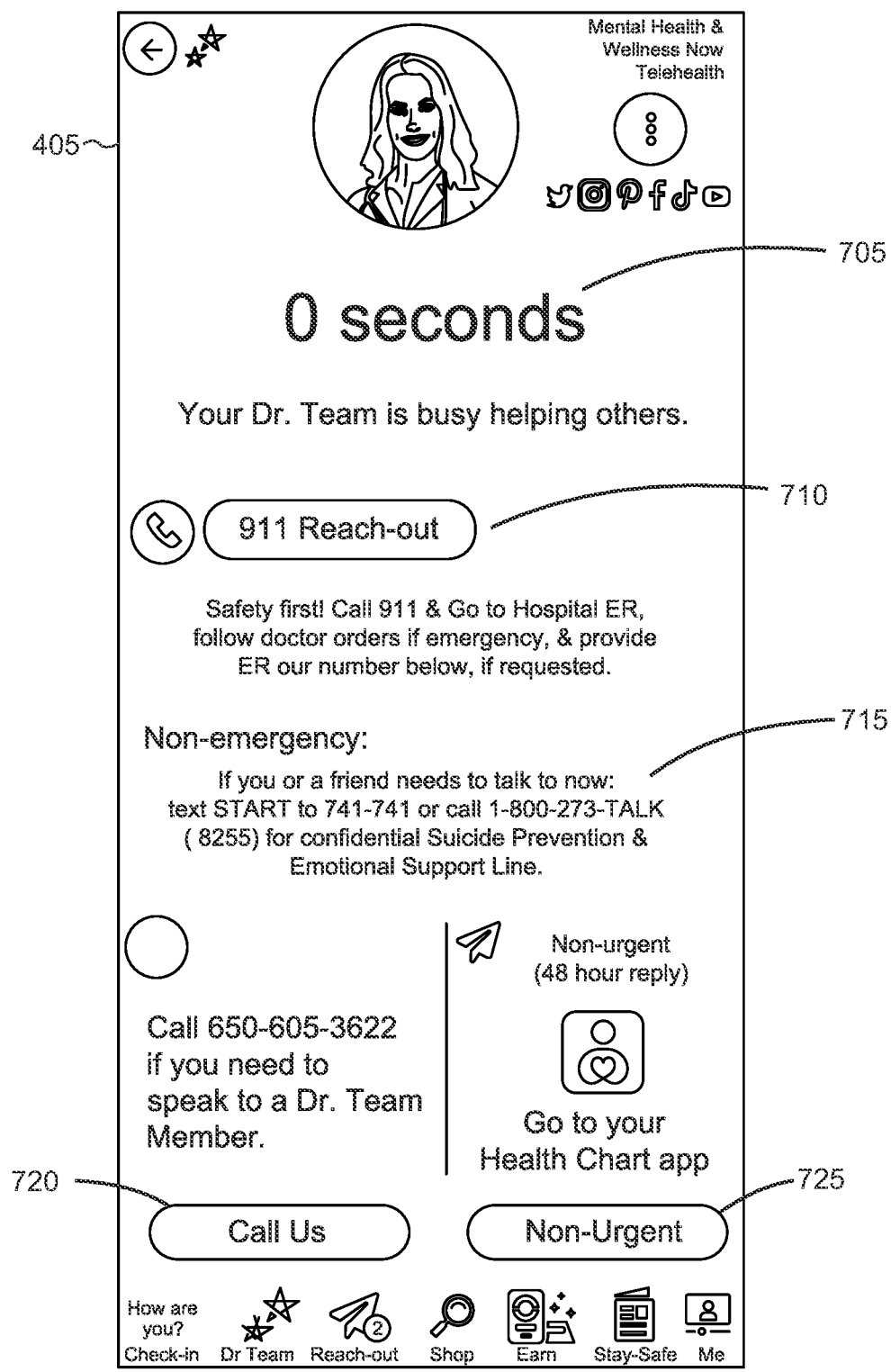
FIG. 7 shows an illustrative user interface in which no-response protocols are initiated.

FIG. 7 shows an illustrative UI in which the countdown timer 705 has reached zero seconds, and the check-in application notifies the user that the medical providers are unavailable. To maintain the severity of the situation, the check-in application provides the user with one or more options to seek help. For example, a 911 reach out 710 button is created that would cause the user's computing device to initiate a phone call. The user is presented with non-emergency emotional support line 715 to communicate with someone via texting or phone. And the user is presented with the ability to call the check-in application's direct helpline for an emergency 720 or utilize an alternate application for non-urgent scenarios 725.

Figure 8:
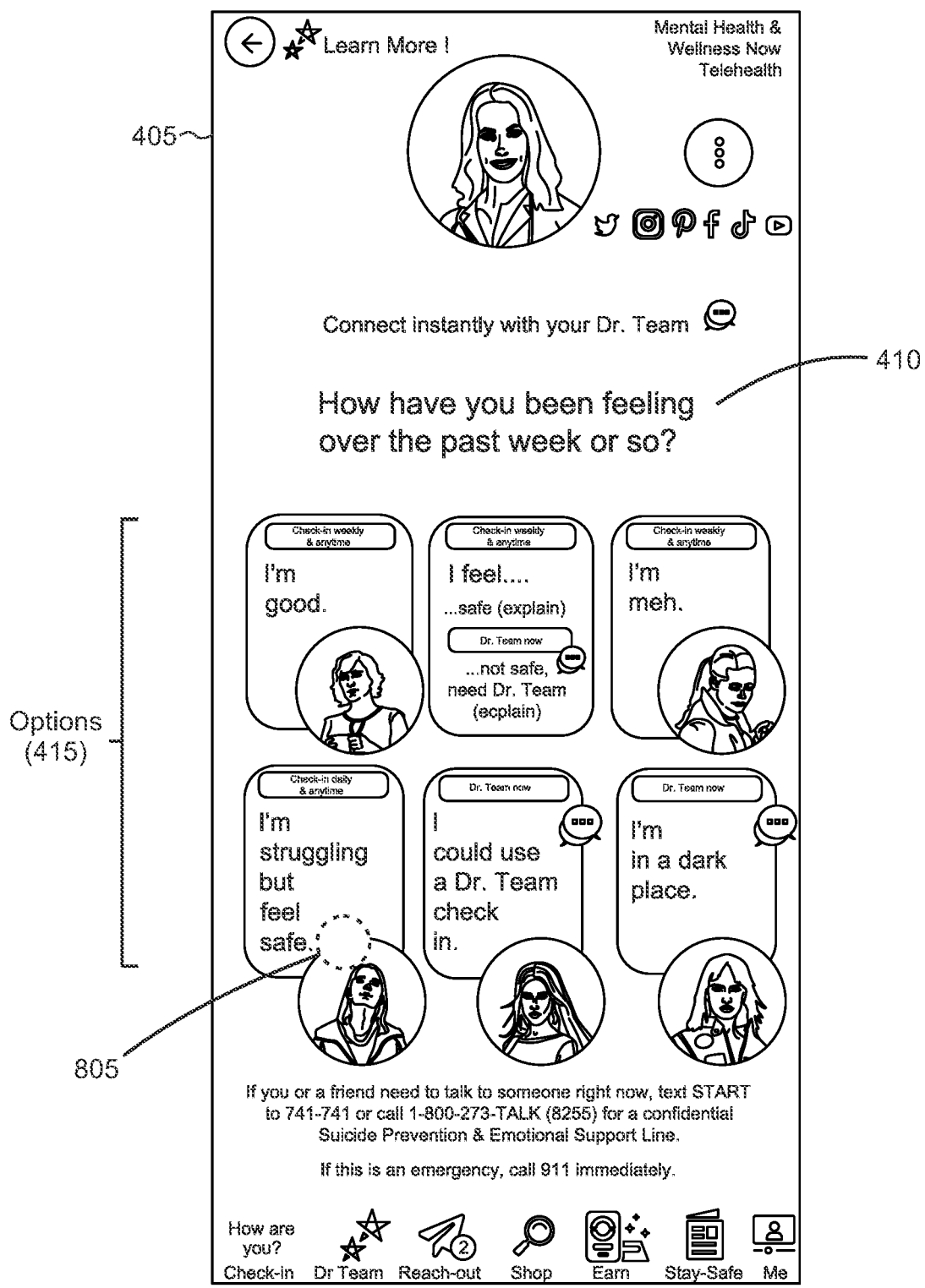
FIG. 8 shows an illustrative user interface in which the check-in application queries the user on their mental health.
Figure 9:
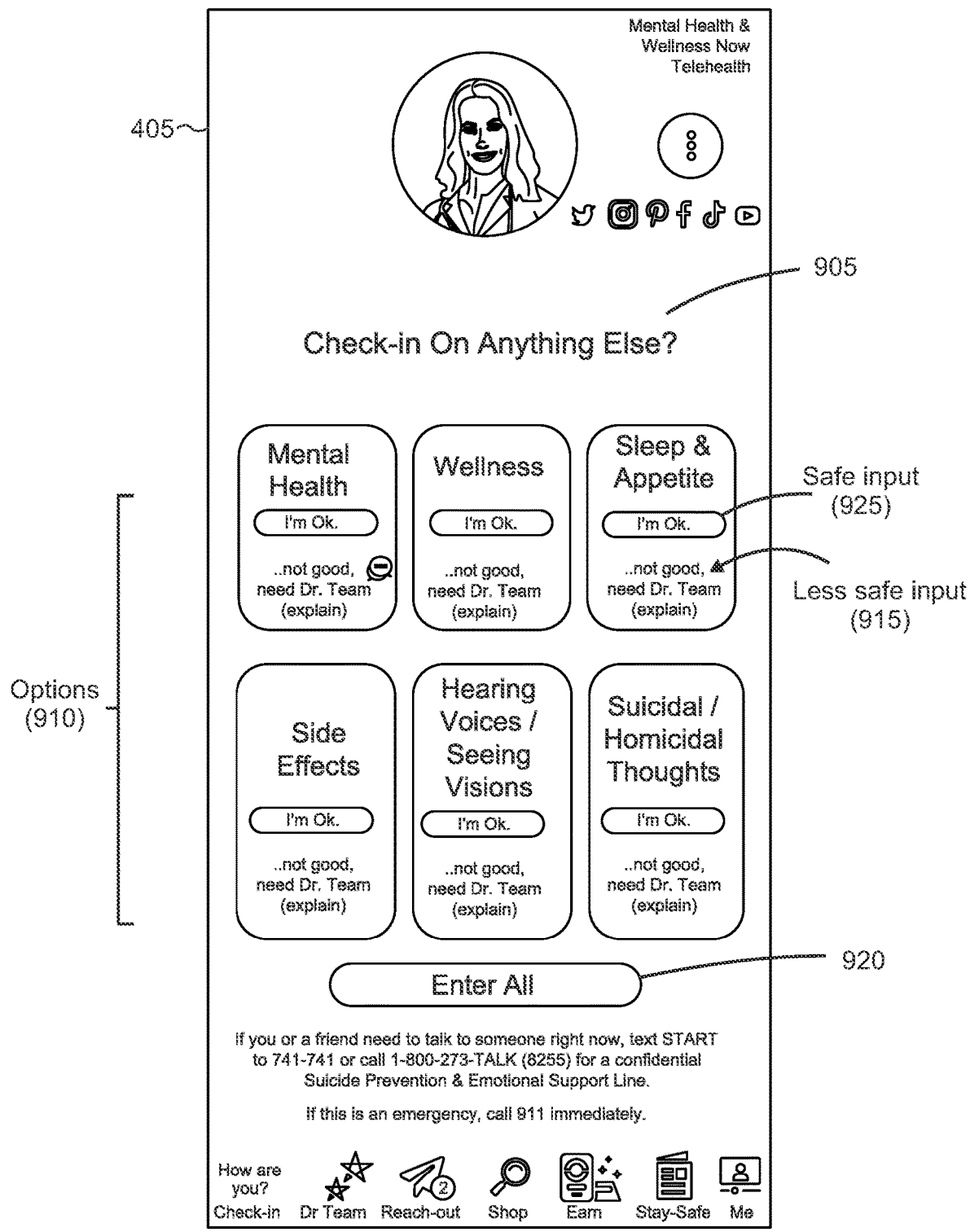
FIG. 9 shows an illustrative user interface in which the check-in application queries the user for any other information.
Figure 10:
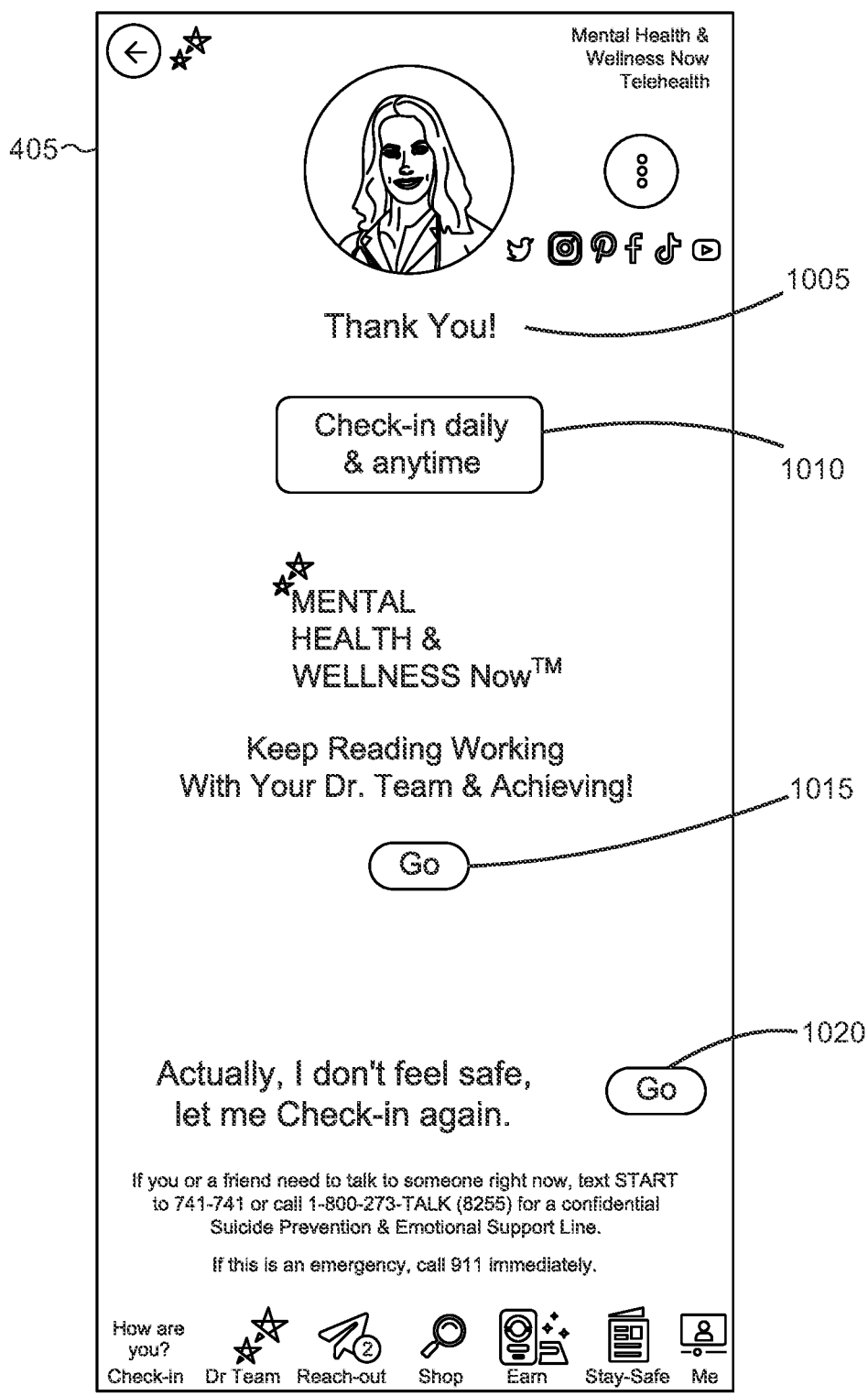

FIGS. 8-10 show illustrative UIs for a medium-severity automated response by the check-in application. FIG. 8 shows an illustrative UI In which the user selects 805 a response associated with medium-severity mental health that the user is struggling with but feels safe. The input may be performed, for example, using a touchscreen display, pointing device, keyboard, voice command, etc. The check-in application may provide the user with various other options 910 to further investigate or elicit additional mental health information from the user before advancing them to the final screen and not flagging the situation as a high-severity health risk. The options presented in FIG. 9 include a safe input 925 and a less safe input 915. These follow-up questions ensure all is being done while the check-in application has the user's attention before approving them to move forward. In some embodiments, the check-in application may require the user to enter input for each of the available options 910 and then force the user to select the "Enter All" 920 button. Alternatively, the user may be provided with the option of answering one or more of the questions presented.

FIG. 10 shows an illustrative UI in which the scenario was ultimately identified as medium-severity. The check-in application thanks 1005 the user, reminds them that they can check in daily and anytime 1010, provides them with a clickable link 1015 to read mental health information to improve their wellbeing, and provides the user with the opportunity to click the link 1020 if the user has decided they don't feel safe again. Clicking the link 1020 may start the process over again (e.g., FIGS. 4 and 8). Alternatively, if the user's answers to the additional options in FIG. 9 indicate that the user is in a high-severity state, then the check-in application may direct the user to the high-severity protocols and response, as shown in FIGS. 5-7.

Figure 11:
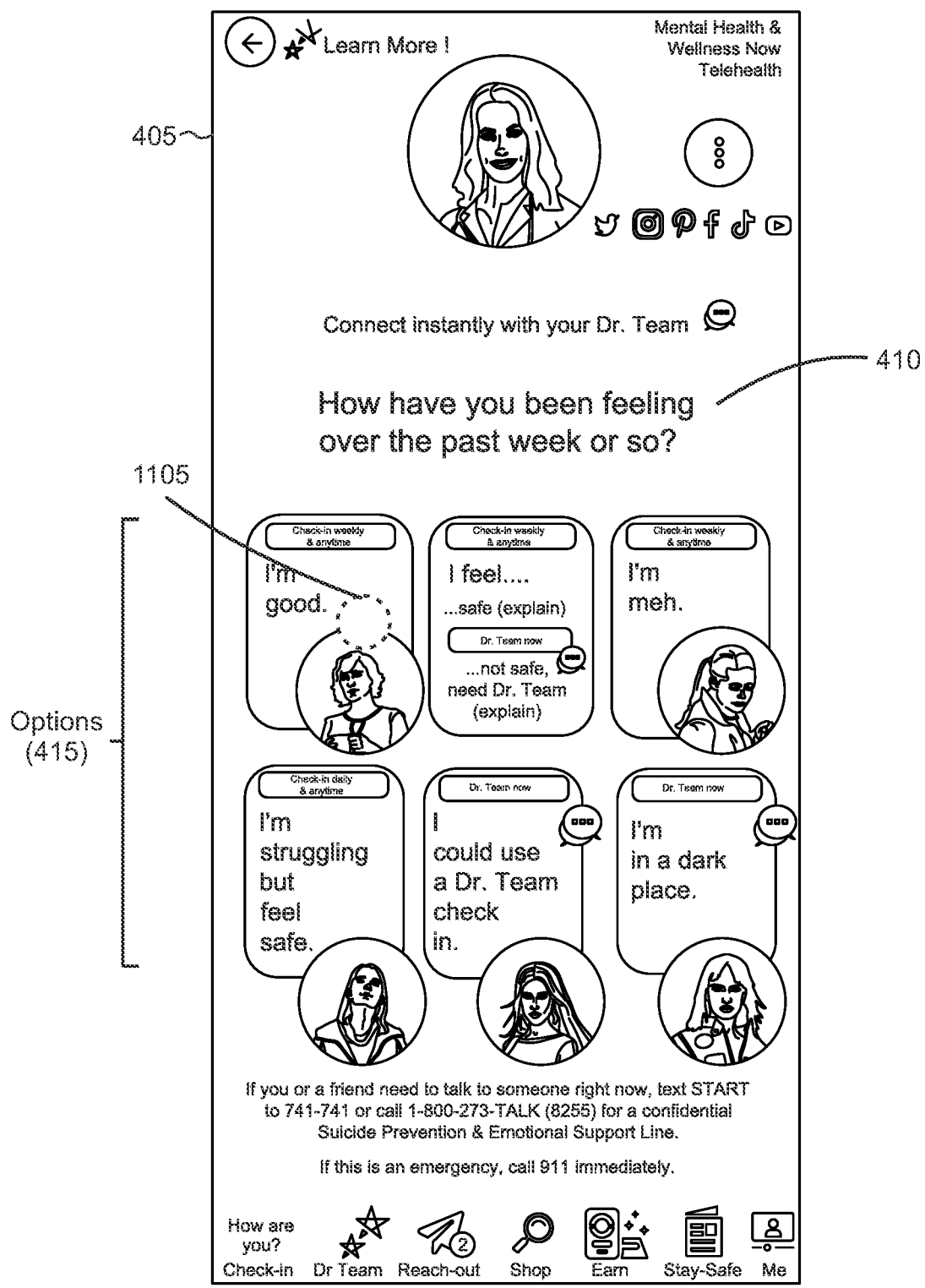
FIG. 11 shows an illustrative user interface in which the check-in application queries the user on their mental health.
Figure 12:
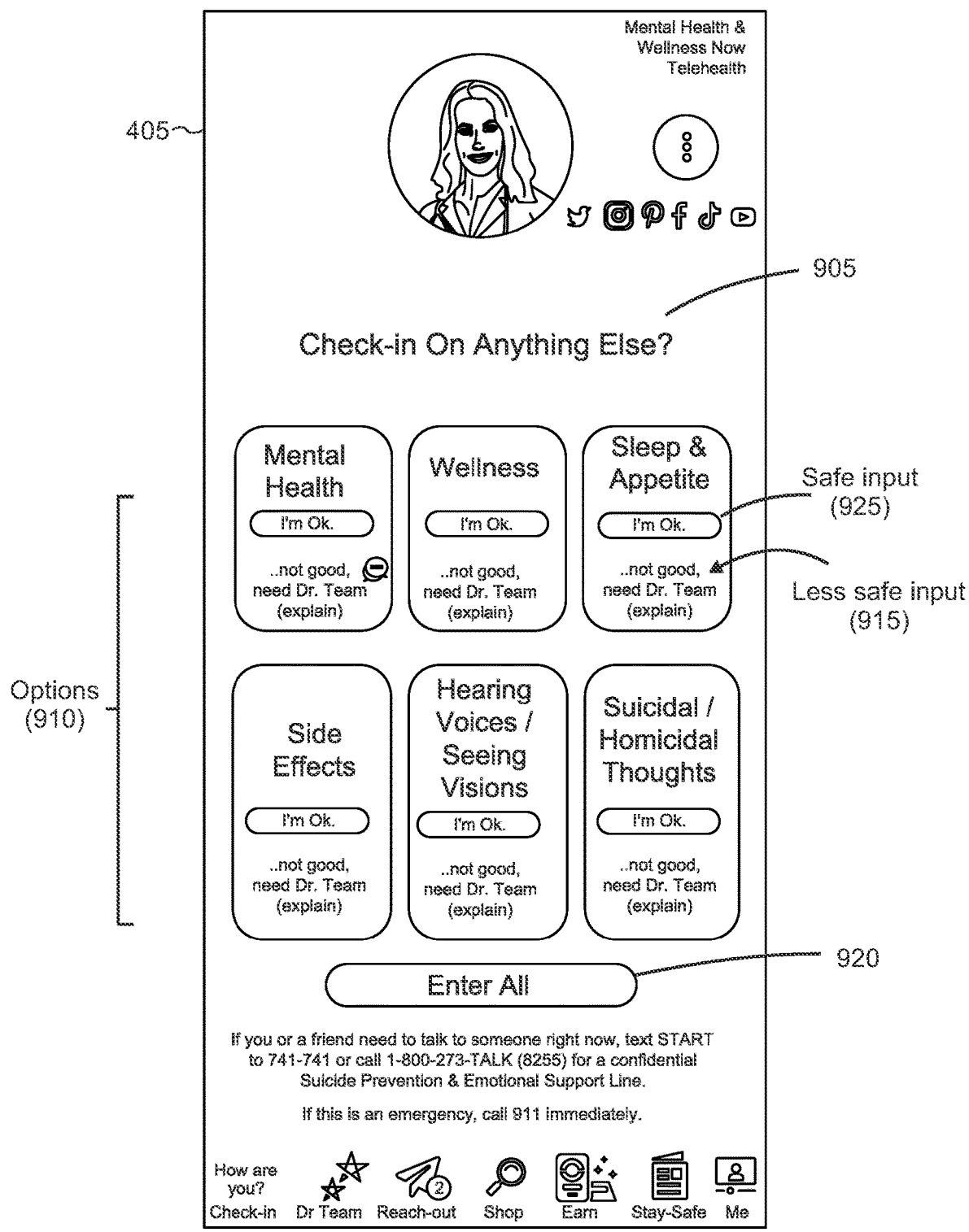
FIG. 12 shows an illustrative user interface in which the check-in application queries the user for any other information.
Figure 13:
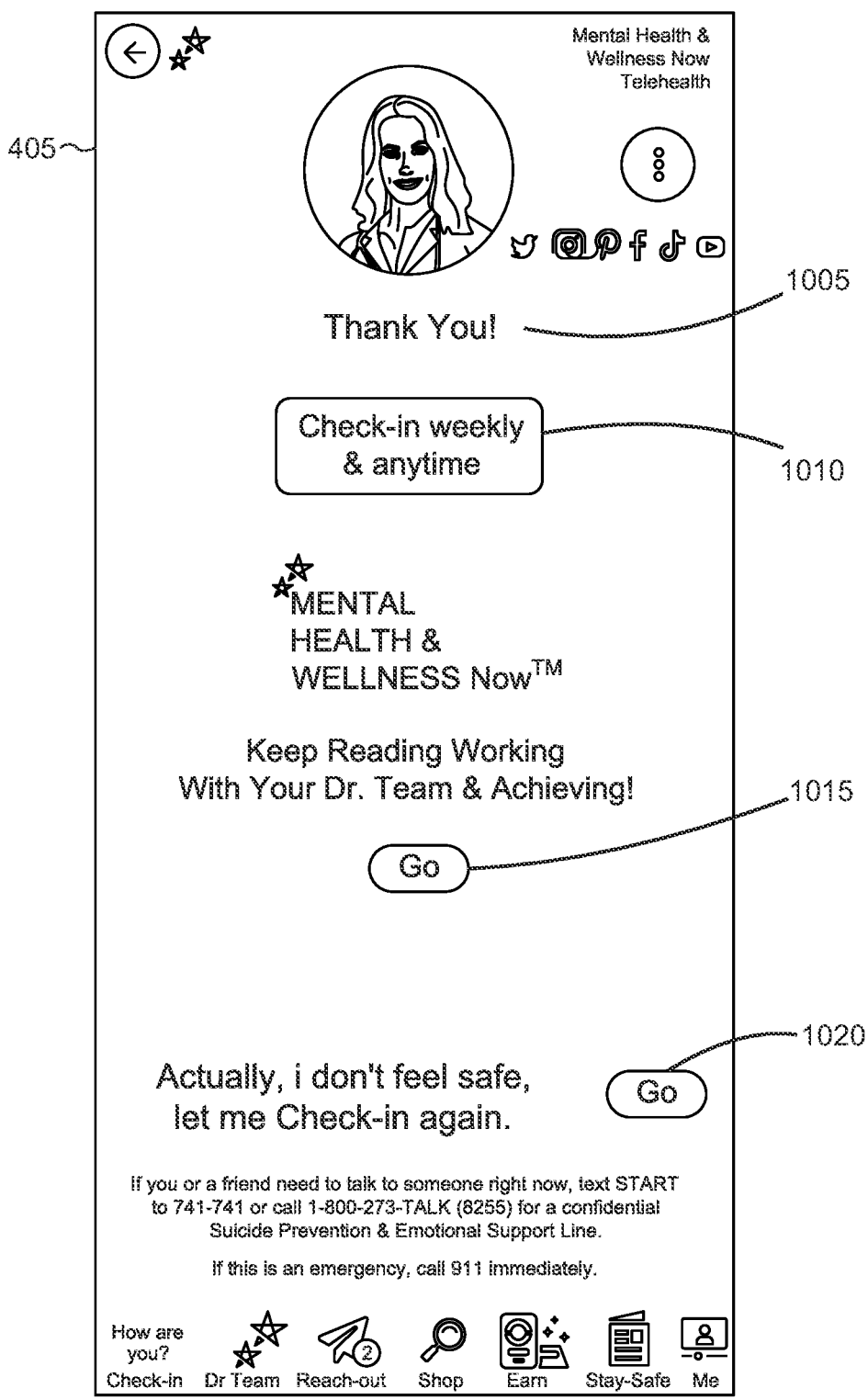

FIGS. 11-13 show illustrative UIs for a low-severity automated response by the check-in application, and FIGS. 12 and 13 are similar to FIGS. 9 and 10 for the medium-severity response. FIG. 11 shows an illustrative UI In which the user selects 1105 a response associated with low-severity mental health, that the user feels "good." The check-in application may provide the user with various other options 910 to further investigate or elicit additional mental health information from the user before advancing them to the final screen and not flagging the situation as a high-severity health risk. The options presented in FIG. 11 include a safe input 925 and a less safe input 915. These follow-up questions ensure all is being done while the check-in application has the user's attention before approving them to move forward. In some embodiments, the check-in application may require the user to enter input for each of the available options 910 and then force the user to select the "Enter All" 920 button. Alternatively, the user may be provided with the option of answering one or more of the questions presented.

FIG. 13 shows an illustrative UI in which the scenario was ultimately identified as low severity. The check-in application thanks 1005 the user, reminds them that they can check in daily and anytime 1010, provides them with a clickable link 1015 to read mental health information to improve their wellbeing, and provides the user with the opportunity to click the link 1020 if the user has decided they don't feel safe again. Clicking the link 1020 may start the process over again (e.g., FIGS. 4, 8, and 11). Alternatively, if the user's answers to the additional options in FIG. 12 indicate that the user is in a high-severity state, then the check-in application may direct the user to the high-severity protocols and response, as shown in FIGS. 5-7.

Figure 14:
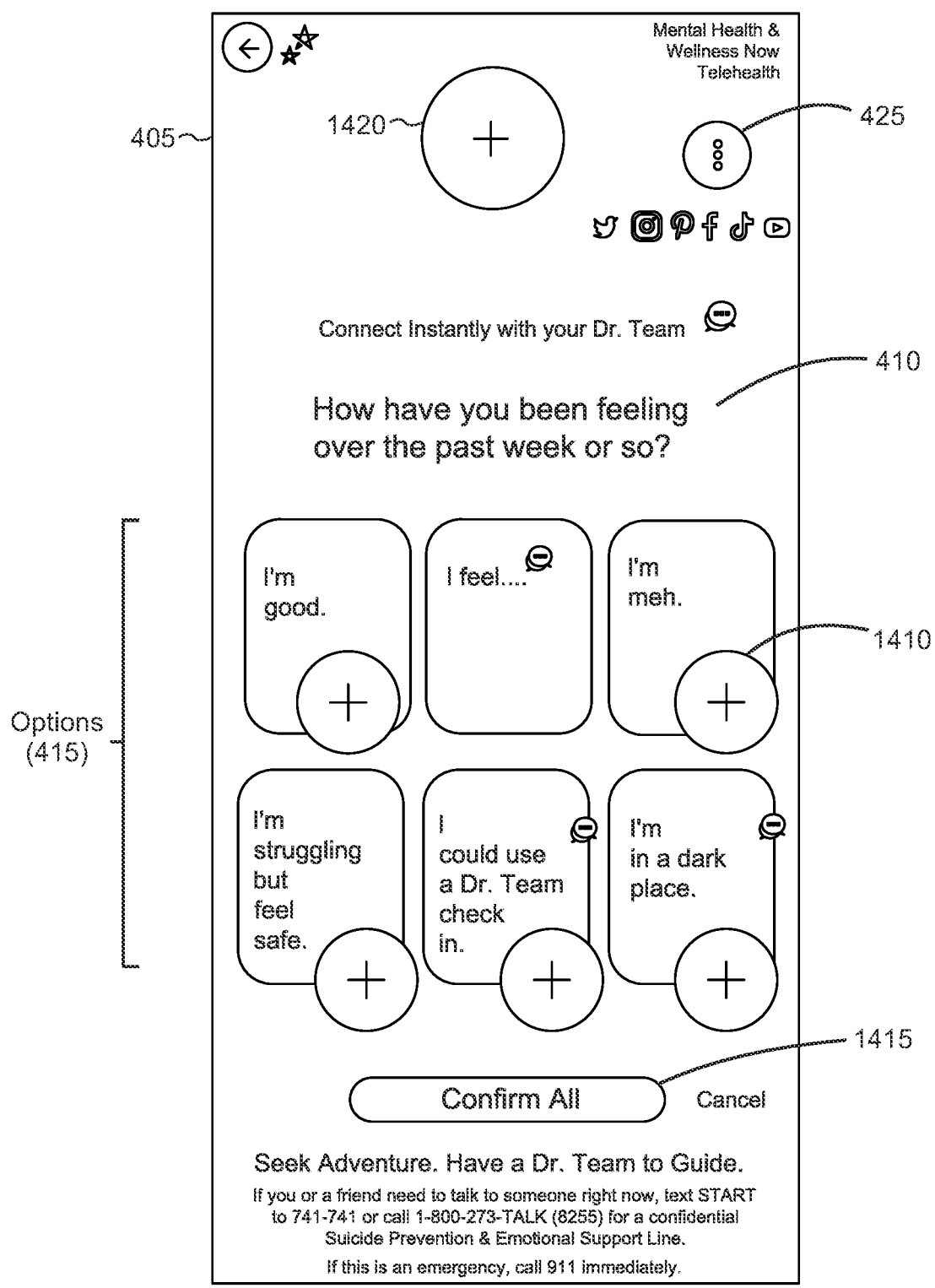
FIG. 14 shows an illustrative user interface in which the check-in application provides the user with the option to input and associate personalized photos for each feeling.
Figure 15:
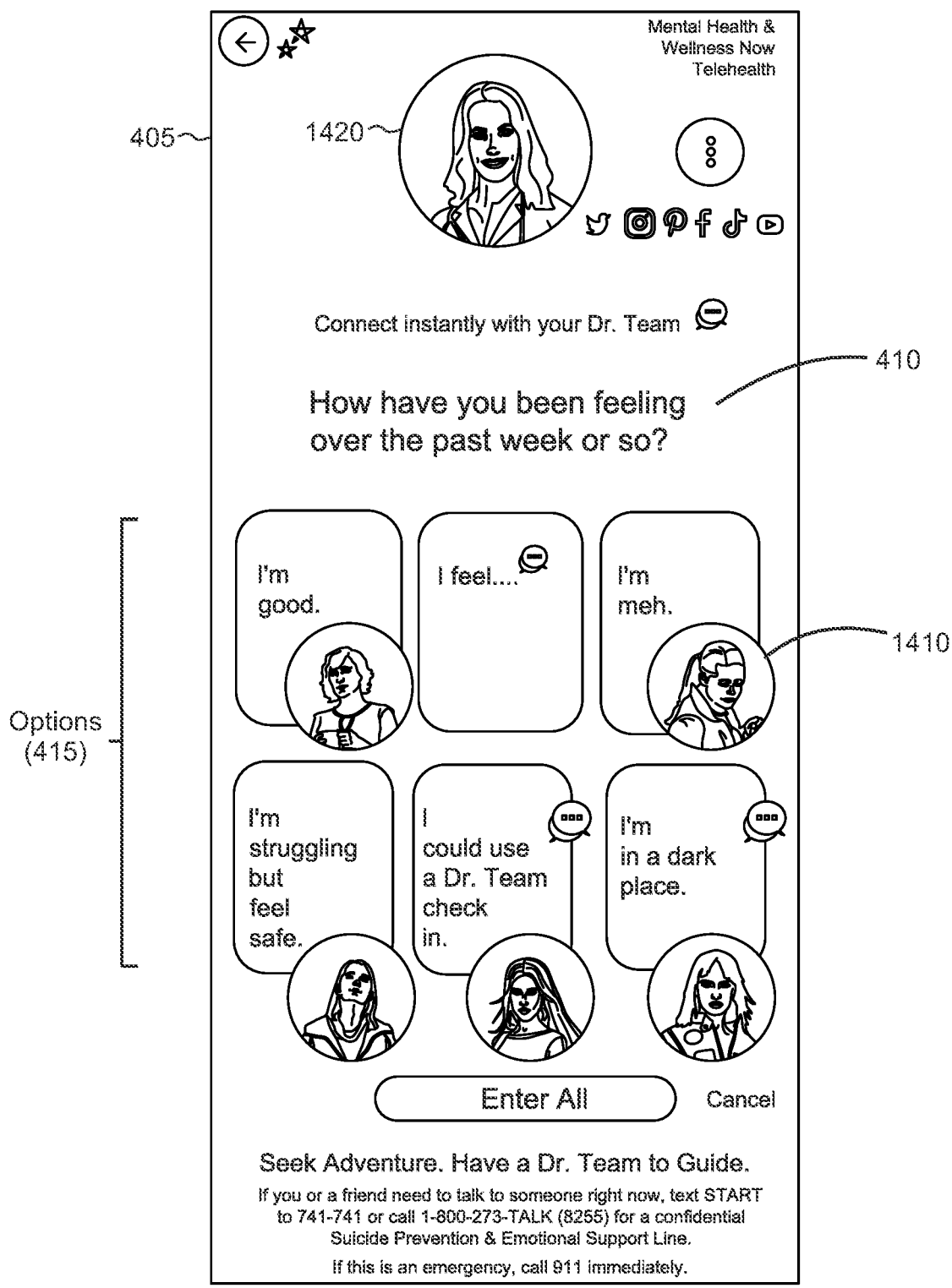
FIG. 15 shows an illustrative user interface in which the check-in application is customized with the user's personalized photos.

FIG. 14 shows an illustrative UI in which the user can personalize the check-in screen for their check-in application. The user may customize and personalize the check-in screen by, for example, selecting the settings icon 425 which provides a drop-down menu for the user to customize the home screen. For example, the user can upload a profile photo to the location 1420 and individually click on the picture areas 1410 to upload a photo for each option 415. The user may, for example, upload a happy or content photo for the "I'm good" option and may upload a sad photo for the "I'm in a dark place" option. FIG. 15 shows an illustrative UI in which the user's personalized photographs are uploaded and associated with each option 415. The picture areas 1410 may come standard with blank spaces that the user can click on to upload their photos, such that anytime they click on the picture areas, the user can either upload or change a photo.

Figure 16:
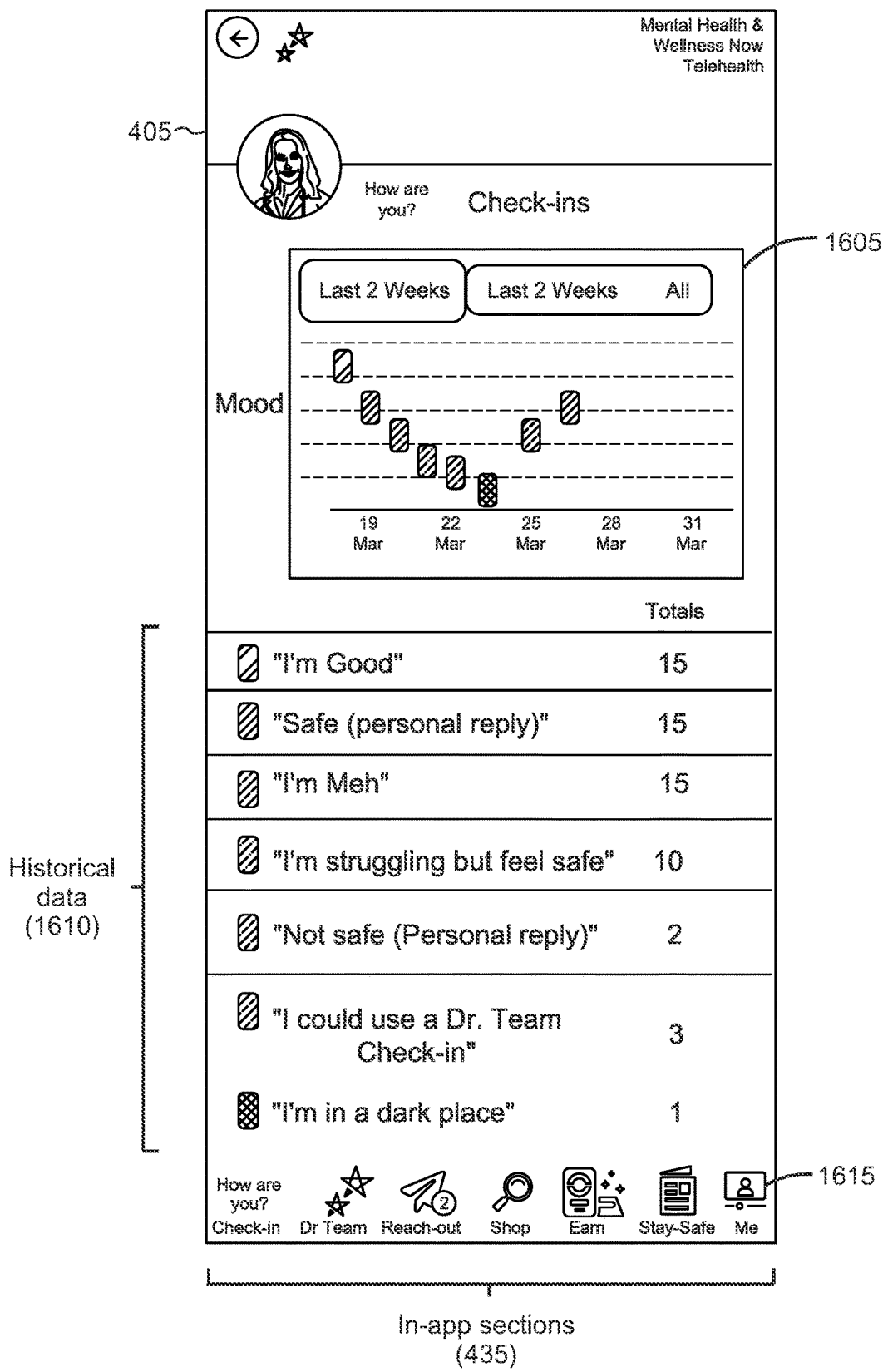
FIG. 16 shows an illustrative user interface in which the user's personalized check-in totals are presented.

FIG. 16 shows an illustrative UI in which historical data 1610 is unique to the user, and a representative graph 1605 is presented. This UI may be responsive to the user selecting the "Me" option 1615 at the bottom in-app sections 435. The user can learn how often they selected the various options 415 on the check-in application's initial check-in screen. Such information can be informative to the user, family, and the medical provider's about the user's overall mental health and wellbeing. Thus, not only does the check-in application provide the capability for immediately helping the user by providing on-call contact to a medical provider, but it also provides a data-driven picture of the user's overall health.

Figure 17:
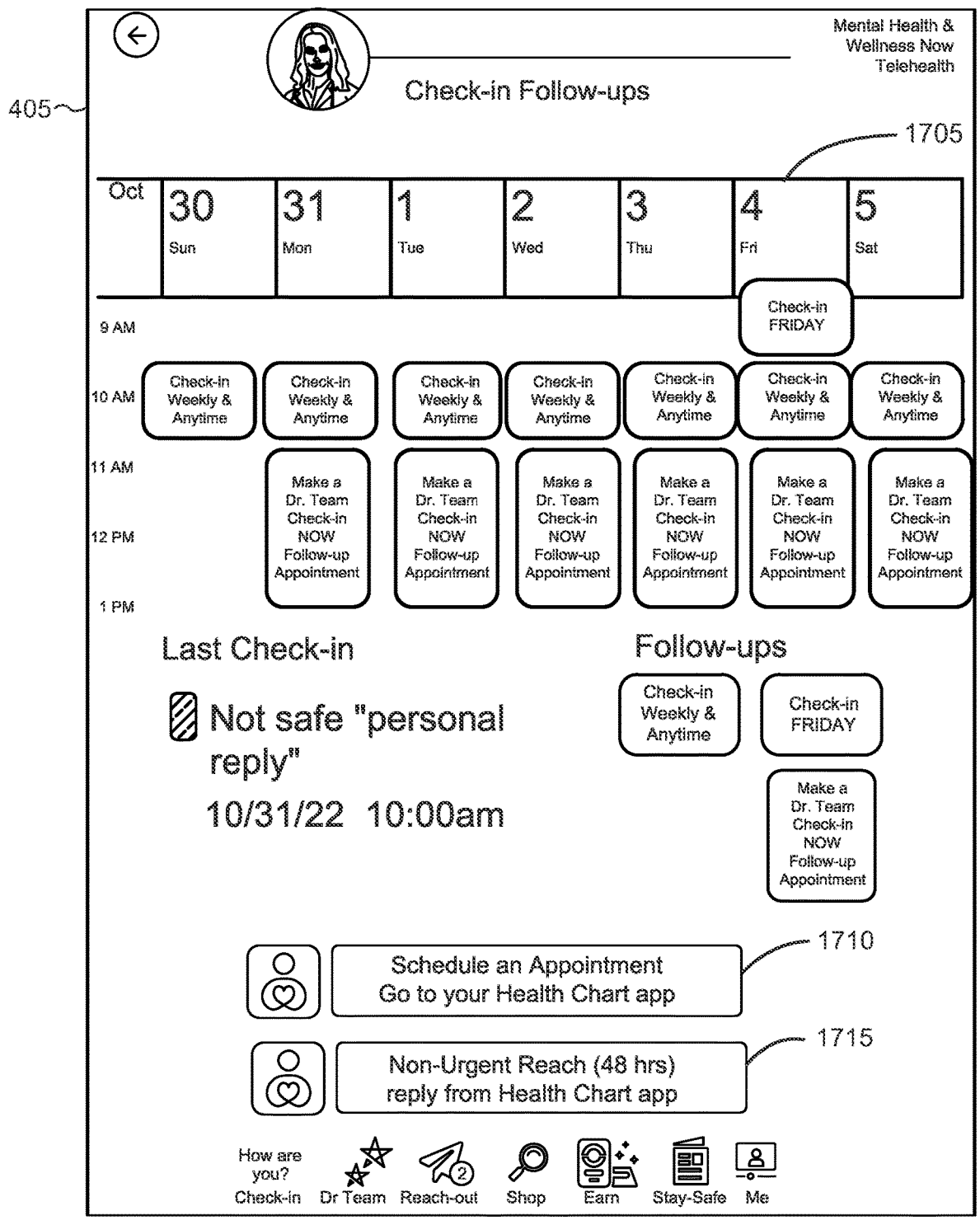

FIG. 17 shows an illustrative UI in which scheduled check-in notifications are programmed into the check-in application's calendar. Alternatively, these check-ins may link to a third-party calendar application, such as Outlook® or Apple® Calendar applications. A Friday check-in is scheduled for every Friday, and the user is also invited to check in daily and weekly anytime while also being invited to call a medical provider at any time. The UI shows the user's last check-in status and lists the "follow-ups" for future check-ins. The UI also enables the user to schedule an appointment for by selecting link 1710, or invites the user for a non-urgent reach out by selecting link 1715.

Figure 18A:
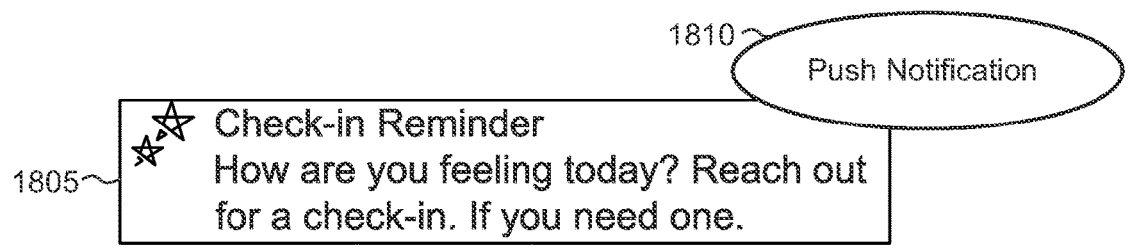
FIGS. 18A-B show illustrative push notifications that may be presented on a user's computing device.
Figure 18B:
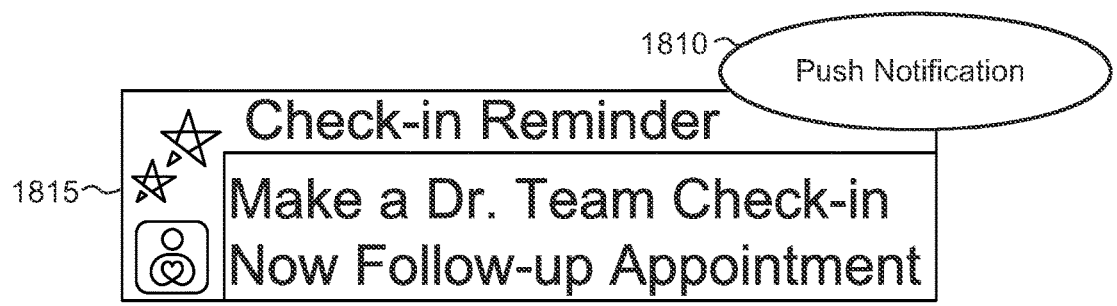

FIGS. 18A and 18B show illustrative push notifications 1810 that may be presented on a user's smartphone device to remind them to check in with the check-in application. The reminders 1805 and 1815 may be specific or unique to the scheduled reminders in the check-in application's calendar portion of the application shown in FIG. 17. Thus, the user may receive a Friday check-in reminder, along with daily reminders for check-ins and medical provider follow-ups.

Figure 19:
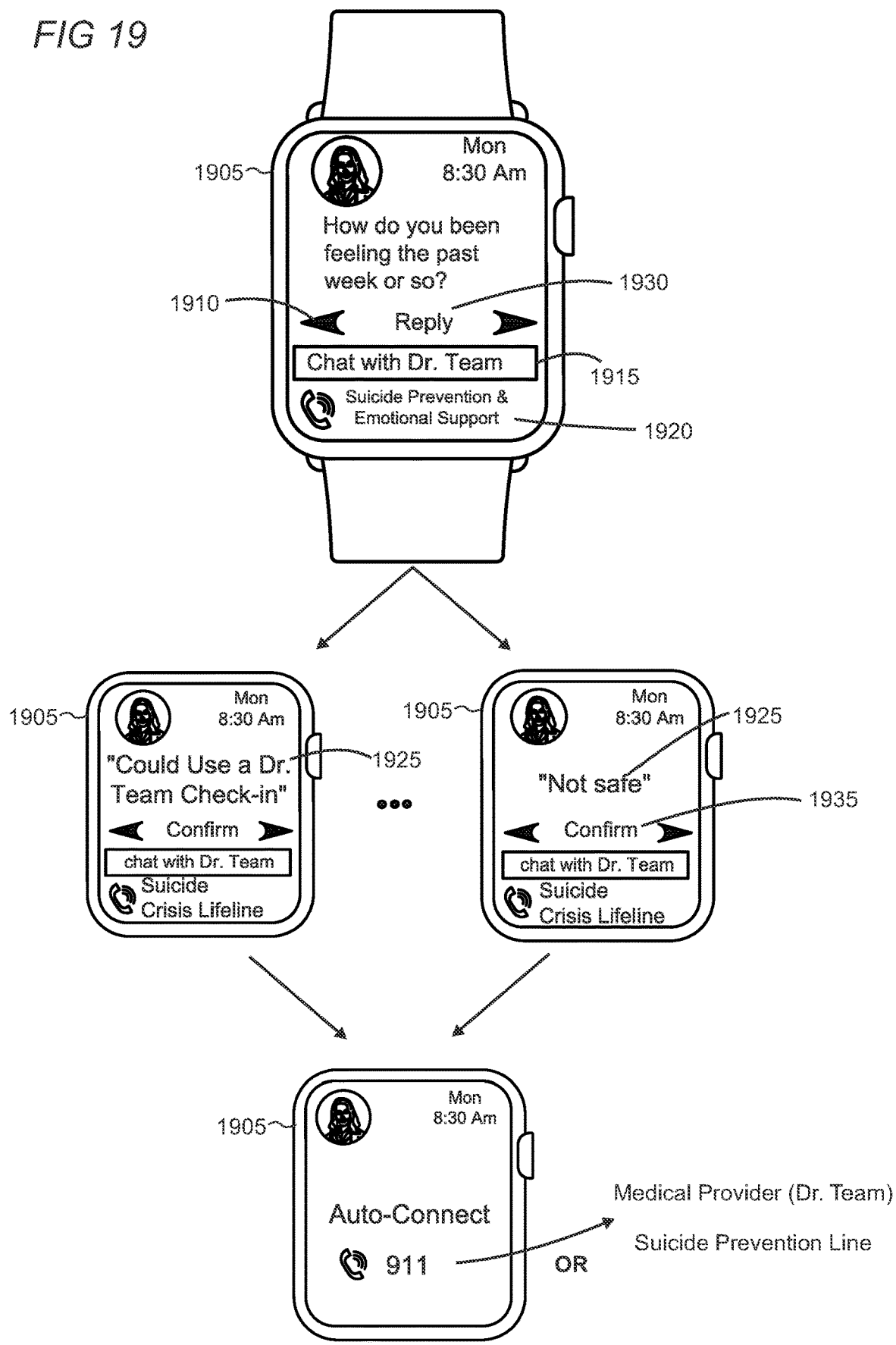
FIGS. 19 and 20 show illustrative user interfaces on a user's periphery smartwatch device.
Figure 20:
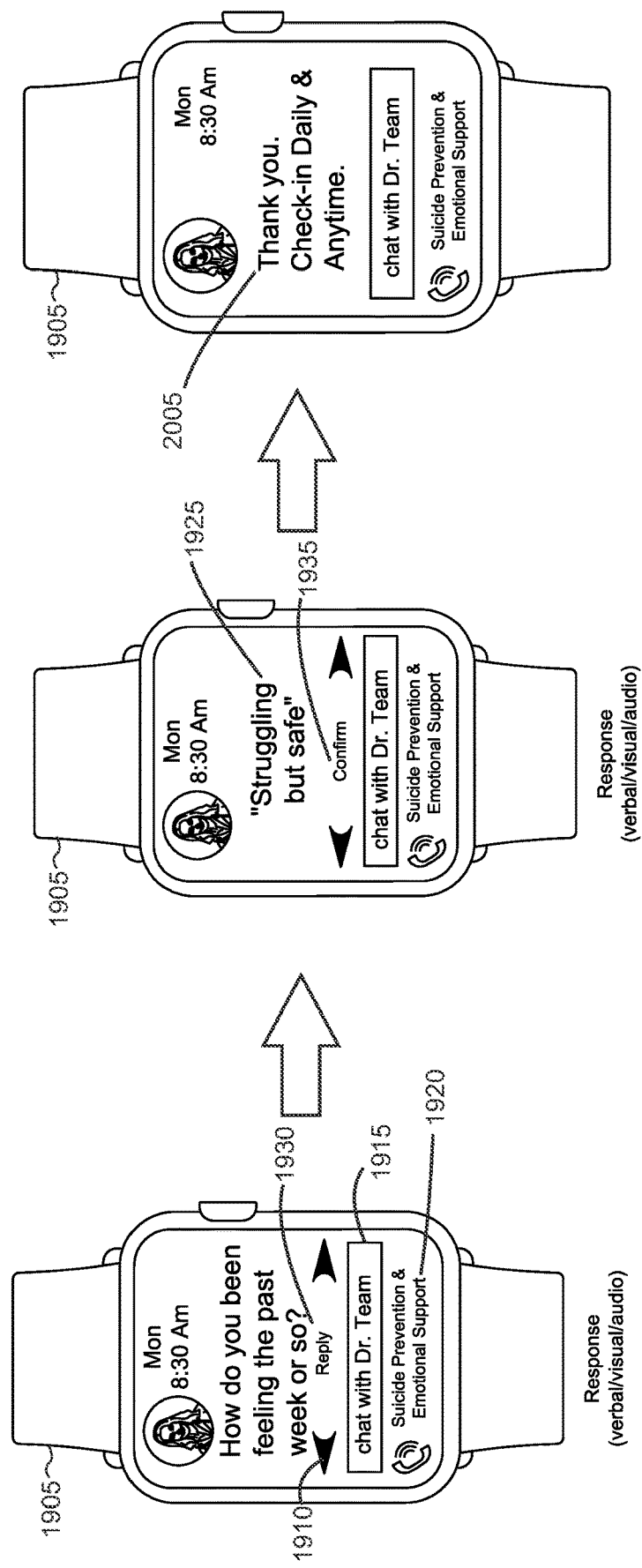

FIGS. 19 and 20 show illustrative implementations of the check-in application configured to operate with a user's peripheral device, such as their smartwatch 1905. While a smartwatch is shown, other types of computing devices and peripheral devices may have a unique adaptation of the check-in application as used on the smartphone device discussed above, such as head mounted display (HMD) devices, among other devices. The processes for the smartwatch may track the automated responses shown and discussed with respect to FIGS. 4-13 above.

FIG. 19 shows an illustrative UI on a smartwatch in which the user is queried as to how they feel. The user can run through the options (e.g., options 415 in FIG. 4) by selecting arrows 1910 and selecting a suitable response 1925. The user may select the "Reply" button and/or scroll the arrows 1910 and then to find a response appropriate for their current mental state. The user can then select the "Confirm" button 1935 to enter their response. The user is initially and continually provided the option to "Chat with Dr. Team" 1915, so they can have an immediate conversation with a medical provider, if necessary. Likewise, the user is initially and continually provided with the option to contact the Suicide Crisis hotline 1925 as an alternate mental health option. Ultimately, in this implementation, the user's smartwatch 1905 auto-connects the user to a provider for immediate help because the situation was identified as high severity. The user may be auto-connected to 911, a medical provider part of Dr. Team, or a suicide prevention hotline. This automated process tracks the process in FIGS. 4-8. Although not shown, a timer countdown may be presented on the UI as well, either before or contemporaneous with the auto-connect functionality.

FIG. 20 shows an illustrative UI on the user's smartwatch 1905 in which a medium severity response is identified based on the user's check-in answers. While a medium severity procedure is shown, a similar overall procedure may be present for a low-severity scenario. Similar to the setup in FIG. 19, the user can select Reply 1930 and then scroll through the options using arrows 1910. In this scenario, the user's responses indicate to the check-in application that the user is in a medium- or low-severity mental state and accordingly implements the respective automated procedures (e.g., FIGS. 9-13). The user has ultimately presented a thank you response and a reminder to check in daily and anytime in 2005. It is noted that the specific user-response for low- and medium-severity responses are distinct, but, at least with respect to the UI in this example, the user may be provided with similar system responses.

Figure 21:
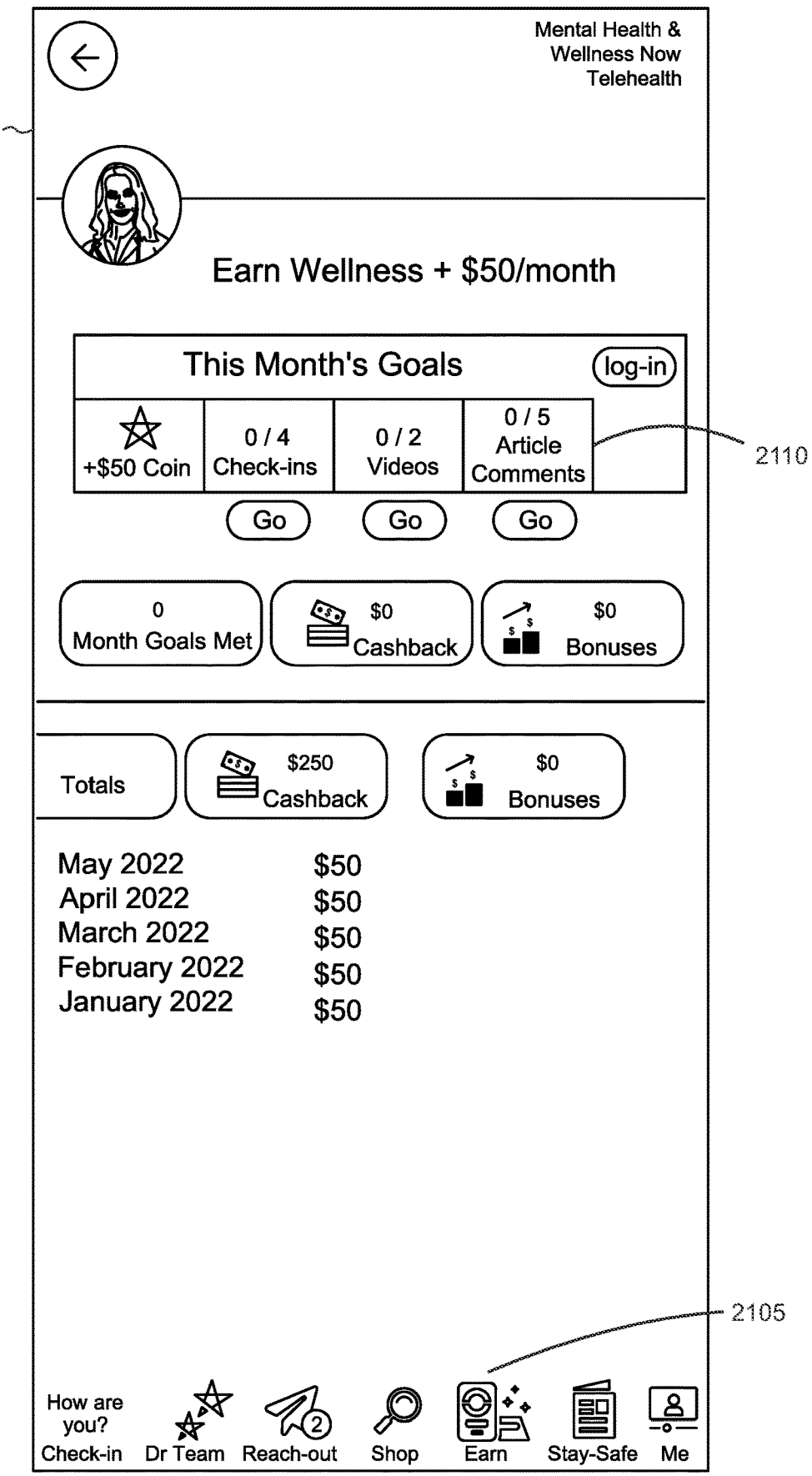
FIG. 21 shows an illustrative user interface of the user's monetary reward totals.

FIG. 21 shows an illustrative UI in which the user's monetary earnings are shown based on their use of the check-in application. This UI may appear responsive to the user selecting the Earn 2105 option at the bottom of the in-app sections 435. This section provides an incentive-based reward system to encourage user use and responses at the check-in application. Rewards, such as financial rewards, may be given based on various uses of the check-in application. For example, the check-in application may reward the user $0.050, $1.00, $5.00, etc. each time the user checks in at one of the options 415 (FIG. 4), reads mental health materials provided (FIG. 10), schedules check-ins using the scheduling feature (FIG. 17), initiates a call, chat, video, or engagement with a medical provider (FIG. 6 or 19), enters follow-up information using options 910 (FIG. 9), among other features.

Alternatively or additionally, the user may receive a set amount of virtual money based on a pre-set minimum interaction with the check-in application, whether time-based (e.g., four hours per month) or click-based (e.g., checks in 10 times per month, clicks through other features 30 times per month, etc.). Such incremental rewards may be logged in the earnings tab of the in-app sections.

As shown in FIG. 21, the rewards section may have a goals section 2110 that logs the number of times the user accesses certain parts of the application each month, such as check-ins, videos, articles or comments, etc. Accessing these portions may lead to the user achieving the $50 reward for that month. The money may be transferred to a respective user via a gift card that is mailed to them or virtually forwarded to them for use since at least some users using the application may not be old enough for a bank account.

Figure 22:
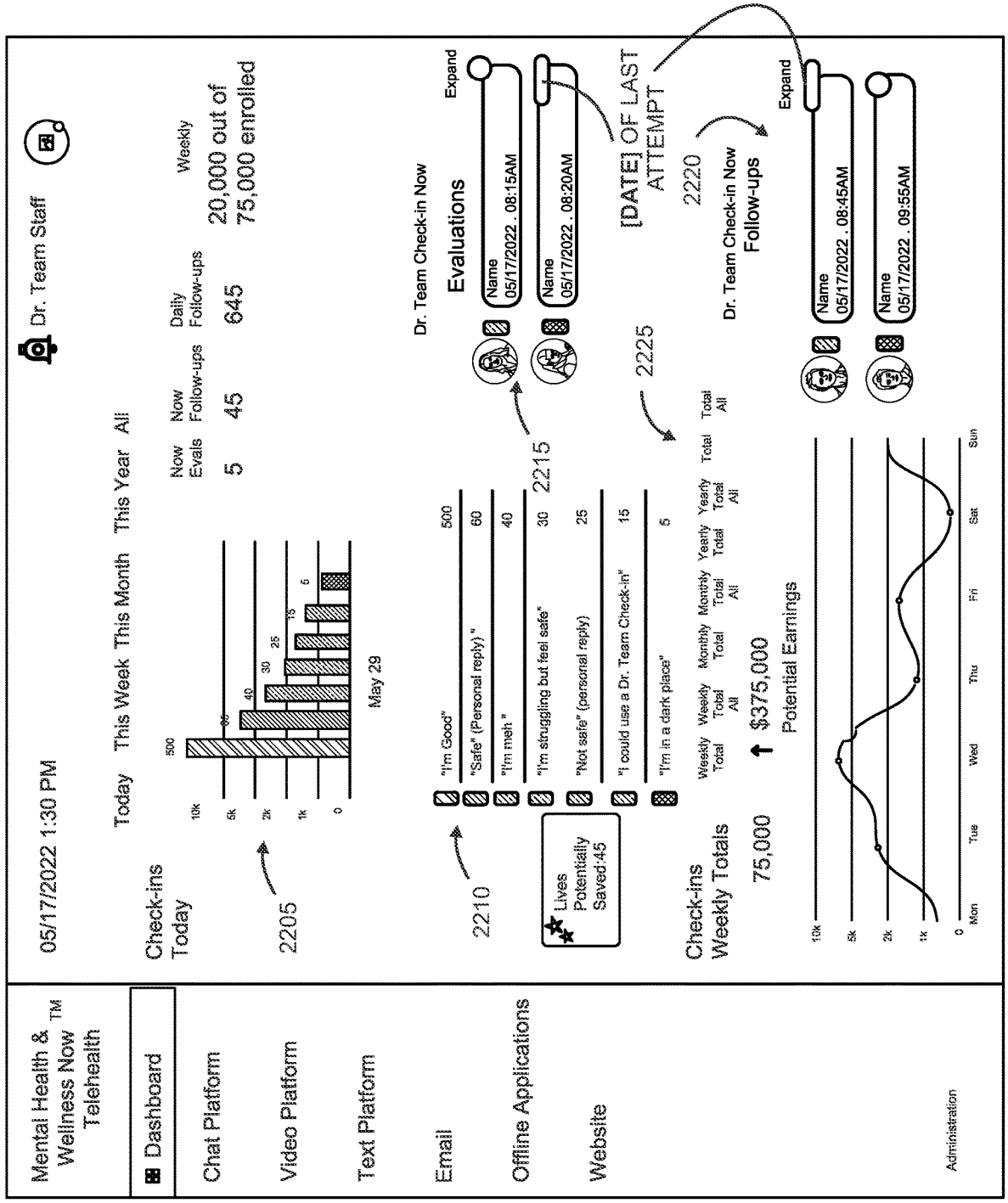
FIG. 22 shows an illustrative user interface of an administrator's backend display.

FIG. 22 shows an illustrative backend user interface that may be utilized by administrators of the check-in application. This backend system may be accessible by, for example, an owner, administrator, medical professional, etc., of the check-in application using a distinct computing device. The backend system provides various data and graphics representative of the total number of users and uses across the check-in application. Data may be anonymized for privacy concerns, but at times the identities of individuals may be known so help can be delivered. As shown, the backend system provides information regarding the number of check-ins over a period of time 2205, a breakdown of the type of responses 2210, user information for medical provider evaluations 2215, and user information for medical provider follow-ups 2220, and "Potential Earnings" of the Dr. Team staff based on the financial information displayed in FIG. 23, discussed below.

Figure 23:
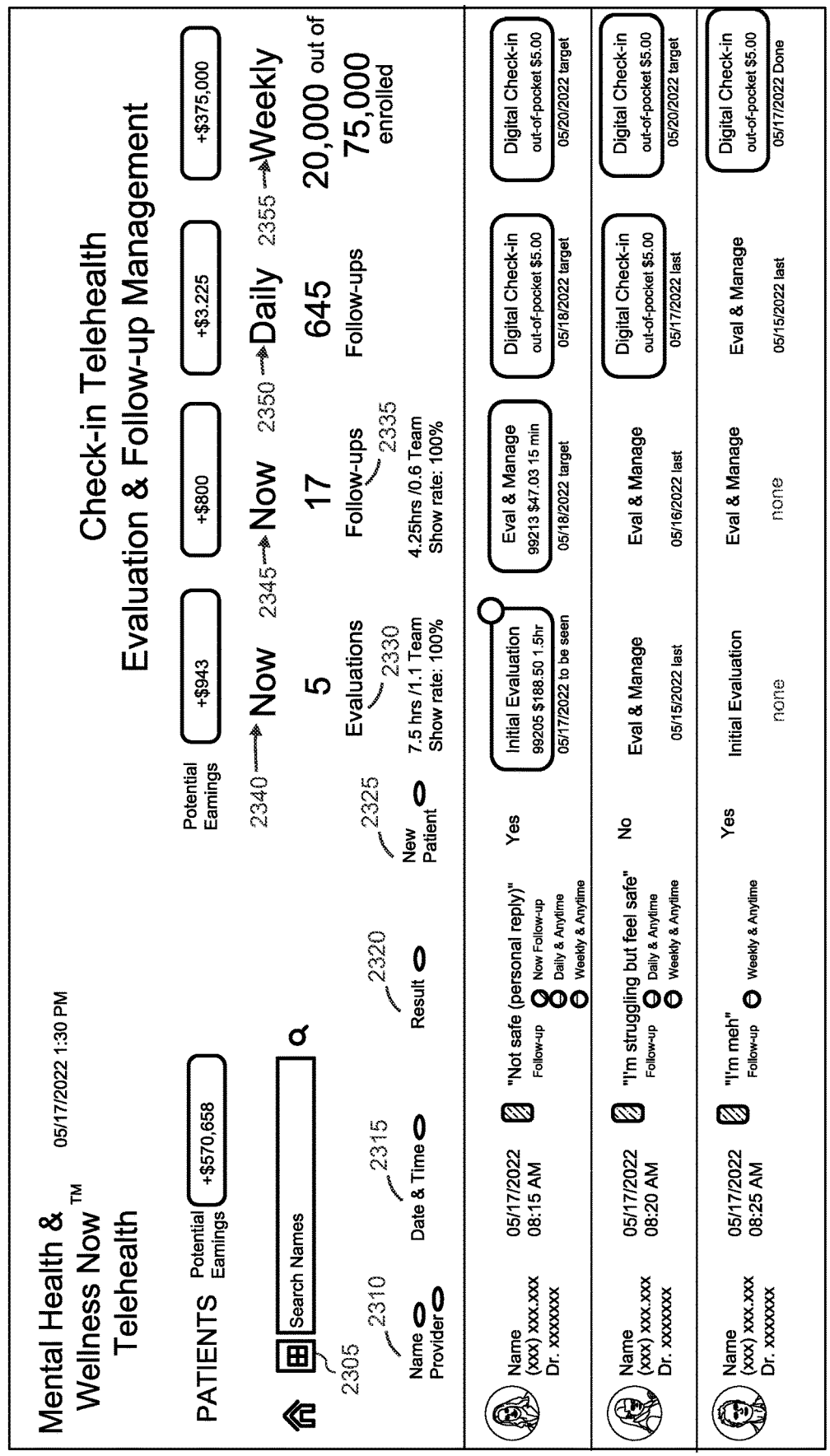

FIGS. 23 and 24 show an additional illustrative backend UI that may be utilized by administrators of the check-in application. The backend administrators, such as Dr. Team staff, employees, etc. can customize the various variables. By clicking a column title or result, a customized patient interface opens, providing further management information and allowing for viewing automatic defaults, custom manual settings per medical provider staff preference, and clinical decision-making. There is an expandable menu 2305 that expands into the left navigational menu. The administration link within this left navigation menu allows for global settings customization. All variable reporting can be sorted and filtered for Dr. Team staff management. For example, the sort function can display various states (not shown) by recent, oldest, last check-in length of time, must follow patient status, and any variable on the GUI report.

The backend system lists the patient's name and medical provider 2310, the date and time of last user response 2315, the result of the last user response 2320 with various follow-up information, whether the patient is a new or existing patient 2325 (which may affect the billing code and whether the patient requires an initial evaluation or follow up evaluation, and evaluation and follow-up information 2330, 2335.

In the evaluation 2330 section, the number of patients awaiting an evaluation is shown. The total time needed to evaluate patients are reported with the total needed medical provider staff necessary and a customized hourly divisor (e.g., seven hours) representing an exemplary workday. A customized show rate is also provided (e.g., 100%) and can be manually adjusted. Each patient's evaluation criteria are displayed with evaluation names (e.g., Initial Evaluation or Evaluation & Management), reimbursement codes (e.g., 99205 or 99213), reimbursement amount (e.g., $188.50 or $188.12 respectively), and time needed (e.g., 1.5 hours). Colors can be used to designate certain information as well, such as colors that designate patients awaiting an evaluation, whether an evaluation was performed with the corresponding date, and status reported underneath, currently being seen with medical provider staff, and last follow-up attempt. In a high severity auto-triaged response, auto-determined care follows.

The Now Evaluations 2340 is auto-triaged and auto-determined, automatically triggering to 'on status' (e.g., yellow toggle status "On") and automatically scheduling: a) Now Follow-up (e.g., 10 a.m. daily notification starting next day following a Now Evaluation); b) Daily Follow-up (e.g., 10 a.m. daily notification starting next day following a Now Evaluation); and c) Weekly Follow-up (e.g., ongoing target date 10 a.m. Friday) target date and time.

The Now Follow-ups 2345 are auto-triaged and auto-determines frequency (e.g., 10 a.m. ongoing daily notification starting the next day following a Now Evaluation) and the number of patients awaiting a follow-up. The total time needed to evaluate patients (e.g., hours) is reported with the total medical provider staff, with a customized hourly divisor (e.g., seven hours) representing an exemplary workday. A customized show rate is also provided (e.g., 100%) and can be manually adjusted. Each patient's evaluation criteria are color-coded with names (e.g., Evaluation & Management), reimbursement codes (e.g., 99213), reimbursement amount (e.g., $47.03), and time needed (e.g., 15 minutes). A color (e.g., grey) designates patients awaiting a follow-up. A color (e.g., black) displays a follow-up performed with the corresponding date and status, currently being seen with medical provider Staff (e.g., round green dot), and last follow-up attempt (e.g., elliptical green dot with date inside as shown in FIG. 22). The backend administrators have the option to switch off the Now follow-ups 2345.

The daily Follow-ups 2350 auto-determines frequency (e.g., scheduled a 10:00 a.m. ongoing daily notification starting the next day following a Now Evaluation and also triggered from a medium severity response automated triage). The number of patients awaiting a follow-up is shown. Each patient's evaluation criteria can be color-coded with associated names (e.g., Digital Check-in), reimbursement codes, reimbursement amount (e.g., out-of-pocket reimbursement), and time. Colors can designate certain information, such as patients that await a follow-up (e.g., grey), blue for a follow-up performed with the corresponding date, and color for status (e.g., last or target date).

In a medium severity, auto-triaged response, auto-determined care is as follows: a) Daily Follow-up (e.g., 10:00 a.m. daily notification starting next day following a Now Evaluation); and b) Weekly Follow-up (e.g., ongoing target date 10:00 a.m. Friday) target date. A repeated severity of response could elevate care. For example, a repeated medium auto-determined triage could increase severity and assignment to a high severity triage with a high severity auto-determined immediate follow-up.

The medical provider staff has clinical discretion to continue Daily Follow-ups or turn them off (by clicking on the patient information. If turned off, a patient will no longer show a color (e.g., grey background) to designate a patient awaiting an evaluation as the status will be off.

Weekly Follow-ups 2355 auto-determined frequency (e.g., low severity response automated triage), and the number of patients awaiting a weekly follow-up is shown. Each patient's evaluation criteria may be color-coded with associated names (e.g., Digital Check-in), reimbursement codes (e.g., reimbursement code), reimbursement amount (e.g., out-of-pocket reimbursement), and time. Colors can be used to designate certain information, such as grey designates patients that await a follow-up, blue represents a follow-up performed with a corresponding date, and a status (e.g., the last or target date is reported underneath. Weekly follow-ups have a target date (e.g., Friday), and the dates may advance weekly.

In a low severity, auto-triaged response, auto-determined care is as follows: a. Weekly Follow-up (e.g., ongoing target date 10 a.m. Friday) target date (time—not shown).

The medical provider staff has clinical discretion to continue weekly follow-ups or turn them off. If turned off, a patient will no longer show a color to designate a patient awaiting an evaluation as the status will be off.

The Last Check-in 2405 column represents an average of the last user check-in response (e.g., in days) for all patients and the last user check-in response for each patient. A non-response by the user may also trigger automatic triage, response, and determination. For example, a setting where a non-response over a pre-set length of time may lead to auto-triage for high severity situations, for follow-up, contact, and intervention. Other pre-set lengths of time may trigger low or medium severity auto-triage responses. This configuration can be combined with any GUI variable. For example, Must Follow Patient 2415 may be combined for close follow-up based on the Last Check-in 2405 since they are higher severity.

The Care Note Scheduled 2410 column represents the status of auto-sending of medical provider staff 'care notes' to patients (which is an evidence-based intervention) and is automated here by the medical provider staff by clicking to send a form or a personalized care note that conveys the medical provider staff cares and are available for patient follow-up.

The Must-Follow Patient 2415 column represents the status of patients that must be followed, which may typically be higher-risk patients within clinical practice. For example, colleges and universities retain lists of students that they are obligated to follow for good and protective care. A setting for a must-follow patient 2415 due to their higher risk status may be high severity auto-triaged for auto-determined high severity care and/or combined with the needed frequency of engagement. For example, this may be combined with a Last Check-in 2405 setting above.

The Therapy 2420 column may be turned on for patients with medium or high severity situations or manually selected, representing the number of patients awaiting a therapy appointment out of the total enrolled. Each patient's appointment criteria are displayed and may be color-coded with name (e.g., Therapy), reimbursement code (e.g., 90834), reimbursement amount (e.g., $141.35), and time (e.g., 45 minutes). Certain colors represent a particular status. For example, grey can represent a patient awaiting a follow-up, green, an appointment performed with the corresponding date and status reported underneath, and a mixed color (e.g., green and grey) represents one out of two appointments scheduled, if applicable. Therapy appointments have a target date (e.g., Friday), and the dates will advance weekly. The current status is displayed and the date. The medical provider staff will be able to report therapy manually and/or through an automated application programming interface (API) with electronic medical record (EMR) software and/or patient self-reporting.

The Meds 2425 (abbreviated Medication) column represents is auto-determined for certain patients, such as those with medium or high severity triaged or manually patient selected. This column represents the number of patients awaiting a medication appointment and the total enrolled. Each patient's appointment criteria are displayed and may be color-coded, which is associated with a name (e.g., Evaluation & Management), reimbursement codes (e.g., 99213), reimbursement amount (e.g., $47.03), and time (e.g., 15 minutes). Certain colors designate certain statuses, for example, grey indicates that a patient awaits a follow-up, light blue represents an appointment performed, with the corresponding date and status reported underneath, and a mixed color (e.g., grey and light blue border) represents one out of two appointments scheduled, if applicable, and a Not Enrolled status may be represented with a grey text and border with white background. A Medication Management appointment may have a target date (e.g., Friday), and the dates will advance weekly. The current status is displayed and the date. The medical provider staff will be able to report coaching manually and/or through an automated application programming interface (API) with electronic medical record (EMR) software and/or patient self-reporting.

The Coaching 2430 column may be auto-determined for certain patients, such as those with low severity triaged or manually selected, and represents the number of patients awaiting a coaching appointment and the total enrolled. Each patient's appointment criteria are color-coded and associated with a name (e.g., Coaching), reimbursement codes, reimbursement amount (e.g., out-of-pocket reimbursement), and time. Certain colors represent certain statuses, for example, grey indicates a patient awaits a follow-up, black indicates an appointment performed, with corresponding date and status reported underneath, and a mixed color (e.g., grey and light black border) indicates one out of two appointments scheduled, if applicable, and a Not Enrolled status may be represented with a grey text and border with white background. The coaching has a target date (e.g., Friday), and the dates will advance weekly. The current status is displayed and the date. The medical provider staff will be able to report therapy manually and/or through an automated application programming interface (API) with electronic medical record (EMR) software and/or patient self-reporting.

For all variables, the color-coding designates patients currently being seen by medical provider Staff (e.g., round green dot) and last follow-up attempt (e.g., elliptical green dot with the date. Across the top is potential earnings totaled and associated with each column, based on the patient information and status reflected within each column.

FIGS. 25 and 26 show illustrative UIs for the backend system managed by system administrators, medical providers, etc. FIG. 26 has been separated from FIG. 25, so the text is of sufficient size to enable readability, but in typical implementations, the information in FIG. 26 may be on the same screen as the information in FIG. 25. This backend screen may populate for a given patient responsive to an administrator or provider selecting any of the information shown in FIGS. 23 and 24 for a given patient, such as a column, a particular patient's status, a name, etc.

The screen is dated and time-stamped on the top left. It incorporates various information from the UIs shown in FIGS. 23-24, such as name and medical provider information, date, time, and result of prior user response (e.g., a check-in response), New Patient, and indicator/button display of Now Evaluation.

The left-side variables and user inputs are based on the user check-in responses, the status of mental health & wellness, and demographic and important information entered by the user during application authentication and prior to user responses to ensure contact data is collected. For example, such user information may be input upon the user creating an account with the check-in application. Additionally or alternatively, this information is collected by the check-in application when the user is checking in at the check-in application (e.g., FIG. 4, 8, or 11). Thus, while creating a username and password, the user may be prompted to enter identifying information, such as name, phone number, etc. A graph is a visual representation of the user's check-in responses totaled according to frequency. On the right side of the screen are medical provider input boxes to document clinical notes submitted in with electronic medical record (EMR) software with date/time stamp and medical provider staff signature. An input box is present to document follow-up contact issues (e.g., no response on chat, no reply on call, no reply to text, e-mail request to contact patient sent, etc.), along with date/time stamp and medical provider staff signature. Another input box is present, which is automatically generated by the check-in application to document status changes (e.g., of all variables including rationale, date/time stamp, and medical provider staff signature, as applicable).

FIG. 26 shows a representation of user inputs and events from the user's check-in response at the check-in application.

FIG. 27 shows an illustrative process that may be implemented by a computing device (e.g., smartphone, tablet, personal computer, laptop, etc.), remote server, or periphery device that may implement the functions and features described herein. In step 2705, a user computing device logs into a unique user's account associated with a check-in application responsive to receiving login credentials from a user. In step 2710, the user computing device renders a first screen of the graphical user interface (GUI) which includes an inquiry regarding the user's mental health status. In step 2715, the user computing device receives a user response to the presented inquiry, in which the user response indicates a current status of the user's mental health. In step 2720, the user computing device, responsive to receiving the user response, determines the severity level of the user response. While the user's local computing device may perform this determination, alternatively, a remote server communicating with the local computing device may make the severity determination. A hybrid approach between the local and remote servers is also possible. In step 2725, the user computing device implements automated procedures at the check-in application based on the determined severity level of the user response. In this regard, the remote server may instruct the local device on what automated procedures to implement, or the local device may be pre-set with such automated protocols. The remote server may, for example, periodically update the automated procedures, in which case the local device may depend on the remote server's instructions.

In step 2730, an administrative computing device stores the use's response and a history of responses. The administrative computing device may be a remote server that is accessible via an administrative staff's computing device, such as a laptop, personal computer, etc. In step 2735, the administrative computing device renders the user response and history of use responses and mental health. In step 2740, the administrative computing device renders evaluation and follow-up information on a per-patient basis.

Figure 28:
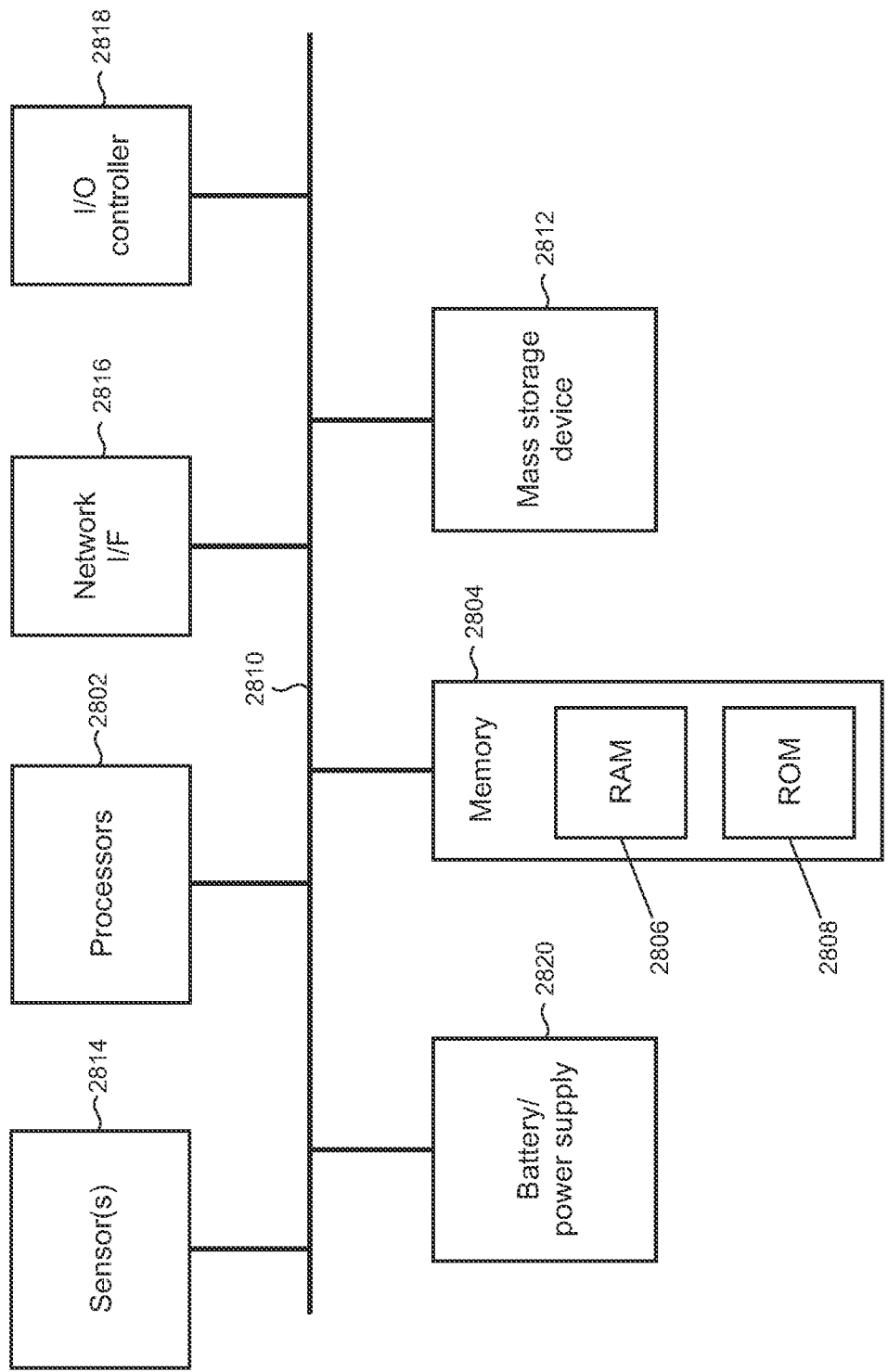
FIG. 28 is a simplified block diagram of an illustrative architecture of a computing device that may be used at least in part to implement the present computing device configured with user check-in for mental health and wellness.

FIG. 28 shows an illustrative diagram of a computer system that may be utilized by the computing device, remote server, periphery device, etc. The architecture 2800 illustrated in FIG. 28 includes one or more processors 2802 (e.g., central processing unit, dedicated Artificial Intelligence chip, graphics processing unit, etc.), a system memory 2804, including RAM (random access memory) 2806, and ROM (read-only memory) 2808, and a system bus 2810 that operatively and functionally couples the components in the architecture 2800. A basic input/output system containing the basic routines that help to transfer information between elements within the architecture 2800, such as during startup, is typically stored in the ROM 2808. The architecture 2800 further includes a mass storage device 2812 for storing software code or other computer-executed code that is utilized to implement applications, the file system, and the operating system. The mass storage device 2812 is connected to the processor 2802 through a mass storage controller (not shown) connected to the bus 2810. The mass storage device 2812 and its associated computer-readable storage media provide non-volatile storage for the architecture 2800. Although the description of computer-readable storage media contained herein refers to a mass storage device, such as a hard disk or CD-ROM drive, it may be appreciated by those skilled in the art that computer-readable storage media can be any available storage media that can be accessed by the architecture 2800.

By way of example, and not limitation, computer-readable storage media may include volatile and non-volatile, removable and non-removable media implemented in any method or technology for storage of information such as computer-readable instructions, data structures, program modules, or other data. For example, computer-readable media includes, but is not limited to, RAM, ROM, EPROM (erasable programmable read-only memory), EEPROM (electrically erasable programmable read-only memory), Flash memory or other solid-state memory technology, CD-ROM, DVD, HD-DVD (High Definition DVD), Blu-ray, or other optical storage, a magnetic cassette, magnetic tape, magnetic disk storage or other magnetic storage device, or any other medium which can be used to store the desired information and which can be accessed by the architecture 2800.

According to various embodiments, the architecture 2800 may operate in a networked environment using logical connections to remote computers through a network. The architecture 2800 may connect to the network through a network interface unit 2816 connected to the bus 2810. It may be appreciated that the network interface unit 2816 also may be utilized to connect to other types of networks and remote computer systems. The architecture 2800 also may include an input/output controller 2818 for receiving and processing input from a number of other devices, including a keyboard, mouse, touchpad, touchscreen, control devices such as buttons and switches, or electronic stylus (not shown in FIG. 28). Similarly, the input/output controller 2818 may provide output to a display screen, user interface, a printer, or other output device types (also not shown in FIG. 28).

It may be appreciated that the software components described herein may, when loaded into the processor 2802 and executed, transform the processor 2802 and the overall architecture 2800 from a general-purpose computing system into a special-purpose computing system customized to facilitate the functionality presented herein. The processor 2802 may be constructed from any number of transistors or other discrete circuit elements, which may individually or collectively assume any number of states. More specifically, the processor 2802 may operate as a finite-state machine in response to executable instructions contained within the software modules disclosed herein. These computer-executable instructions may transform the processor 2802 by specifying how the processor 2802 transitions between states, thereby transforming the transistors or other discrete hardware elements constituting the processor 2802.

Encoding the software modules presented herein also may transform the physical structure of the computer-readable storage media presented herein. The specific transformation of physical structure may depend on various factors in different implementations of this description. Examples of such factors may include but are not limited to, the technology used to implement the computer-readable storage media, whether the computer-readable storage media is characterized as primary or secondary storage, and the like. For example, if the computer-readable storage media is implemented as semiconductor-based memory, the software disclosed herein may be encoded on the computer-readable storage media by transforming the physical state of the semiconductor memory. For example, the software may transform the state of transistors, capacitors, or other discrete circuit elements constituting the semiconductor memory. The software also may transform the physical state of such components in order to store data thereupon.

As another example, the computer-readable storage media disclosed herein may be implemented using magnetic or optical technology. In such implementations, the software presented herein may transform the physical state of magnetic or optical media when the software is encoded therein. These transformations may include altering the magnetic characteristics of particular locations within given magnetic media. These transformations also may include altering the physical features or characteristics of particular locations within given optical media to change the optical characteristics of those locations. Other transformations of physical media are possible without departing from the scope and spirit of the present description, with the foregoing examples provided only to facilitate this discussion.

The architecture 2800 may further include one or more sensors 2814 or a battery or power supply 2820. The sensors may be coupled to the architecture to pick up data about an environment or a component, including temperature, pressure, etc. Exemplary sensors can include a thermometer, accelerometer, smoke or gas sensor, pressure sensor (barometric or physical), light sensor, ultrasonic sensor, gyroscope, among others. The power supply may be adapted with an AC power cord or a battery, such as a rechargeable battery for portability.

In light of the above, it may be appreciated that many types of physical transformations take place in the architecture 2800 in order to store and execute the software components presented herein. It also may be appreciated that the architecture 2800 may include other types of computing devices, including wearable devices, handheld computers, embedded computer systems, smartphones, PDAs, and other types of computing devices known to those skilled in the art. It is also contemplated that the architecture 2800 may not include all of the components shown in FIG. 28, may include other components that are not explicitly shown in FIG. 28, or may utilize an architecture completely different from that shown in FIG. 28.

Figure 29:
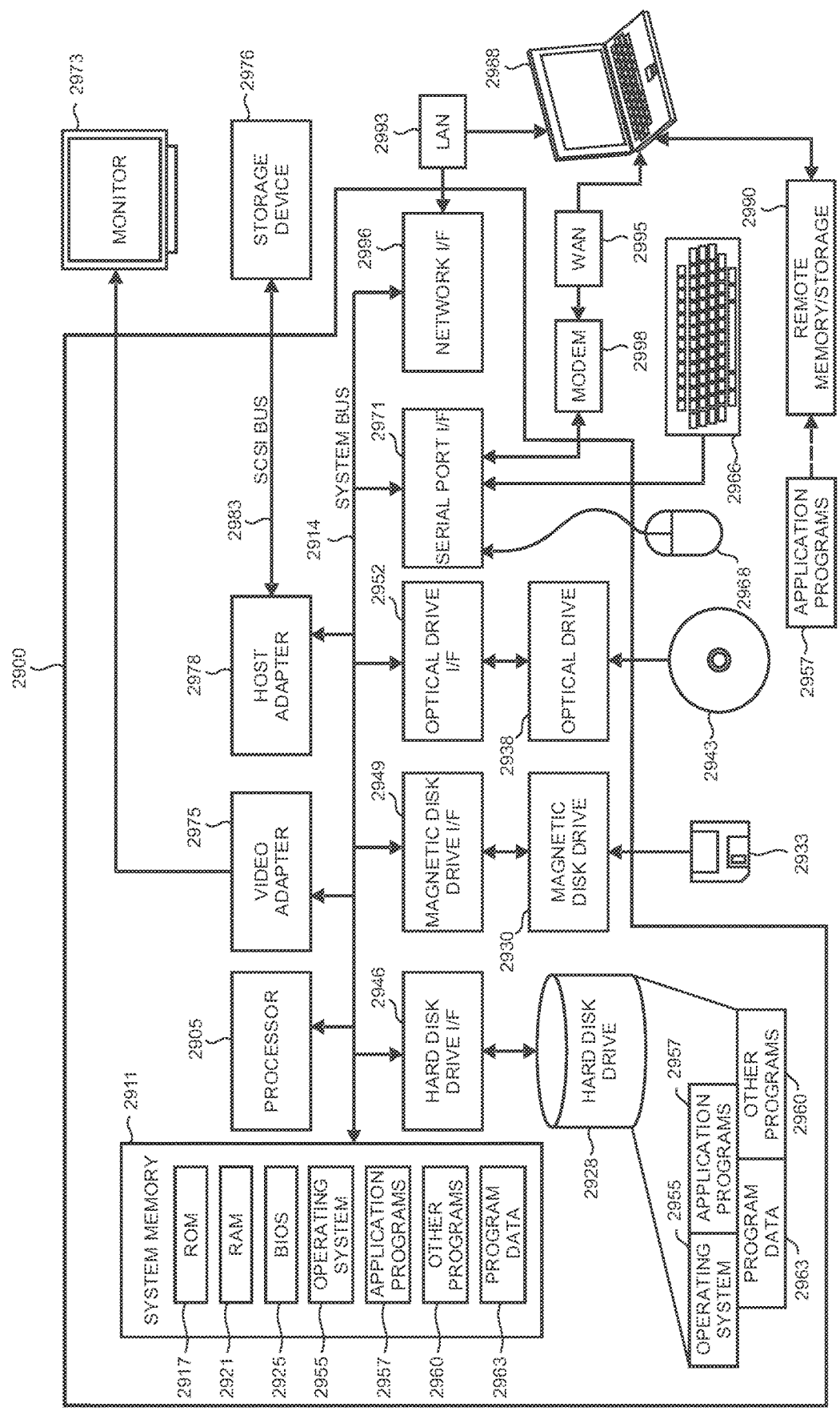
FIG. 29 is a simplified block diagram of an illustrative remote computing device, remote service, or computer system that may be used in part to implement the present computing device configured with user check-in for mental health and wellness.

FIG. 29 is a simplified block diagram of an illustrative computer system 2900 such as a smartphone, PC (personal computer), laptop computer, or server with which the present computing device configured with user check-in for mental health and wellness may be implemented.

Computer system 2900 includes a processor 2905, a system memory 2911, and a system bus 2914 that couples various system components including the system memory 2911 to the processor 2905. The system bus 2914 may be any of several types of bus structures, including a memory bus or memory controller, a peripheral bus, or a local bus using any of a variety of bus architectures. The system memory 2911 includes read-only memory (ROM) 2917 and random-access memory (RAM) 2921. A basic input/output system (BIOS) 2925, containing the basic routines that help to transfer information between elements within the computer system 2900, such as during startup, is stored in ROM 2917. The computer system 2900 may further include a hard disk drive 2928 for reading from and writing to an internally disposed hard disk (not shown), a magnetic disk drive 2930 for reading from, or writing to a removable magnetic disk 2933 (e.g., a floppy disk), and an optical disk drive 2938 for reading from or writing to a removable optical disk 2943 such as a CD (compact disc), DVD (digital versatile disc), or other optical media. The hard disk drive 2928, magnetic disk drive 2930, and optical disk drive 2938 are connected to the system bus 2914 by a hard disk drive interface 2946, a magnetic disk drive interface 2949, and an optical drive interface 2952, respectively. The drives and their associated computer-readable storage media provide non-volatile storage of computer-readable instructions, data structures, program modules, and other data for the computer system 2900. Although this illustrative example includes a hard disk, a removable magnetic disk 2933, and a removable optical disk 2943, other types of computer-readable storage media which can store data that is accessible by a computer such as magnetic cassettes, Flash memory cards, digital video disks, data cartridges, random access memories (RAMs), read-only memories (ROMs), and the like may also be used in some applications of the present computing device configured with user check-in for mental health and wellness. In addition, as used herein, the term computer-readable storage media includes one or more instances of a media type (e.g., one or more magnetic disks, one or more CDs, etc.). For purposes of this specification and the claims, the phrase "computer-readable storage media" and variations thereof are intended to cover non-transitory embodiments and do not include waves, signals, and/or other transitory and/or intangible communication media.

A number of program modules may be stored on the hard disk, magnetic disk 2933, optical disk 2943, ROM 2917, or RAM 2921, including an operating system 2955, one or more application programs 2957, other program modules 2960, and program data 2963. A user may enter commands and information into the computer system 2900 through input devices such as a keyboard 2966 and pointing device 2968 such as a mouse. Other input devices (not shown) may include a microphone, joystick, gamepad, satellite dish, scanner, trackball, touchpad, touchscreen, touch-sensitive device, voice-command module or device, user motion or user gesture capture device, or the like. These and other input devices are often connected to the processor 2905 through a serial port interface 2971 that is coupled to the system bus 2914 but may be connected by other interfaces, such as a parallel port, game port, or universal serial bus (USB). A monitor 2973 or other type of display device is also connected to the system bus 2914 via an interface, such as a video adapter 2975. In addition to the monitor 2973, personal computers typically include other peripheral output devices (not shown), such as speakers and printers. The illustrative example shown in FIG. 29 also includes a host adapter 2978, a Small Computer System Interface (SCSI) bus 2983, and an external storage device 2976 connected to the SCSI bus 2983.

The computer system 2900 is operable in a networked environment using logical connections to one or more remote computers, such as a remote computer 2988. The remote computer 2988 may be selected as another personal computer, a server, a router, a network PC, a peer device, or other common network node, and typically includes many or all of the elements described above relative to the computer system 2900, although only a single representative remote memory/storage device 2990 is shown in FIG. 29. The logical connections depicted in FIG. 29 include a local area network (LAN) 2993 and a wide area network (WAN) 2995. Such networking environments are often deployed, for example, in offices, enterprise-wide computer networks, intranets, and the Internet.

When used in a LAN networking environment, the computer system 2900 is connected to the local area network 2993 through a network interface or adapter 2996. When used in a WAN networking environment, the computer system 2900 typically includes a broadband modem 2998, network gateway, or other means for establishing communications over the wide area network 2995, such as the Internet. The broadband modem 2998, which may be internal or external, is connected to the system bus 2914 via a serial port interface 2971. In a networked environment, program modules related to the computer system 2900, or portions thereof, may be stored in the remote memory storage device 2990. It is noted that the network connections shown in FIG. 29 are illustrative, and other means of establishing a communications link between the computers may be used depending on the specific requirements of an application of the present computing device configured with user check-in for mental health and wellness.

Various exemplary embodiments are disclosed herein. In one exemplary embodiment, implemented is a system that utilizes a check-in application for rendering a graphical user interface (GUI) that enables a user to input updates to their mental health status, comprising: a user computing device, comprising: log in to a unique user's account associated with the check-in application responsive to receiving login credentials from a user; render a first screen of the GUI which includes an inquiry regarding the user's mental health status; receive a user response to the presented inquiry, in which the user response indicates a current status of the user's mental health; responsive to receiving the user response, determine a severity level of the user response; implement automated procedures at the check-in application based on the determined severity level of the user response, in which the automated procedures includes rendering a second screen that addresses and is unique to the user's severity level; and an administrative computing device configured with back-end access to the check-in application's system, comprising: storing at least the user response and a history of user responses; rendering at least the user response and the history of user responses and mental health information; and rendering evaluation and follow-up information for administration on a per-patient basis which is at least in part affected by the user response.

As another example, the check-in application renders a number of patients awaiting evaluation and follow-ups, in which multiple follow-up columns are rendered which focus on differing temporal parameters. In another example, the severity level includes low severity level, medium severity level, or high severity level, and wherein the severity level affects the rendered evaluation and follow-up information. As another example, further comprising: rendering, at the administrative computing device, potential earnings for the administration, in which the potential earnings are rendered on a same screen as the evaluation and follow-up information. As another example, further comprising: rendering, at the administrative computing device, treatment information for multiple patients, in which the treatment information includes at least therapy and coaching in distinct columns. In another example, the treatment information further includes coaching in a distinct column. As another example, further comprising: receiving, at the administrative computing device, user input that selects a patient; and responsive to receiving the user input, rendering, at the administrative computing device, information specific to that patient, in which the information includes diagrams representing historical user check-in responses and administration notes about the patient.

In another exemplary embodiment, disclosed is a method for rendering a graphical user interface (GUI) that enables a user to input updates to their mental health status, comprising: logging, at a user computing device, in to a unique user's account associated with the check-in application responsive to receiving login credentials from a user; rendering, at a user computing device, a first screen of the GUI which includes an inquiry regarding the user's mental health status; receiving, at a user computing device, a user response to the presented inquiry, in which the user response indicates a current status of the user's mental health; responsive to receiving the user response, determining, at a user computing device, a severity level of the user response; implementing, at a user computing device, automated procedures at the check-in application based on the determined severity level of the user response, in which the automated procedures includes rendering a second screen that addresses and is unique to the user's severity level; storing, at an administrative computing device, at least the user response and a history of user responses; rendering, at an administrative computing device, at least the user response and the history of user responses and mental health information; and rendering, at an administrative computing device, evaluation and follow-up information for administration on a per-patient basis which is at least in part affected by the user response.

As another example, the check-in application renders a number of patients awaiting evaluation and follow-ups, in which multiple follow-up columns are rendered which focus on differing temporal parameters. As another example, the severity level includes low severity level, medium severity level, or high severity level, and wherein the severity level affects the rendered evaluation and follow-up information. In another example, further comprising: rendering, at the administrative computing device, potential earnings for the administration, in which the potential earnings are rendered on a same screen as the evaluation and follow-up information. In another example, further comprising: rendering, at the administrative computing device, treatment information for multiple patients, in which the treatment information includes at least therapy and coaching in distinct columns. In another example, the treatment information further includes coaching in a distinct column. As another example, further comprising: receiving, at the administrative computing device, user input that selects a patient; and responsive to receiving the user input, rendering, at the administrative computing device, information specific to that patient, in which the information includes diagrams representing historical user check-in responses and administration notes about the patient.

As another exemplary embodiment, disclosed is one or more hardware-based non-transitory computer-readable memory devices disposed in one or more computing devices, the computer-readable instructions, when executed by one or more processors, cause the one or more computing devices to: log in to a unique user's account associated with the check-in application responsive to receiving login credentials from a user; render a first screen of the GUI which includes an inquiry regarding the user's mental health status; receive a user response to the presented inquiry, in which the user response indicates a current status of the user's mental health; responsive to receiving the user response, determine a severity level of the user response; implement automated procedures at the check-in application based on the determined severity level of the user response, in which the automated procedures includes rendering a second screen that addresses and is unique to the user's severity level; store at least the user response and a history of user responses; render at least the user response and the history of user responses and mental health information; and render evaluation and follow-up information for administration on a per-patient basis which is at least in part affected by the user response.

In another example, the check-in application renders a number of patients awaiting evaluation and follow-ups, in which multiple follow-up columns are rendered which focus on differing temporal parameters. As another example, the severity level includes low severity level, medium severity level, or high severity level, and wherein the severity level affects the rendered evaluation and follow-up information. As another example, the executed instructions further cause the one or more computing devices to: render potential earnings for the administration, in which the potential earnings are rendered on a same screen as the evaluation and follow-up information. In another example, further comprising: rendering, at the administrative computing device, treatment information for multiple patients, in which the treatment information includes at least therapy and coaching in distinct columns. As another example, the treatment information further includes coaching in a distinct column.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed:

1. A system that utilizes a check-in application for rendering a graphical user interface (GUI) that enables a user to input updates to their mental health status, comprising:
   a user computing device, comprising:
      log in to a unique user's account associated with the check-in application responsive to receiving login credentials from a user;

render a first screen of the GUI which includes an inquiry regarding the user's mental health status to initiate a check-in process;
receive a user response to the presented inquiry, in which the user response indicates a current status of the user's mental health;
responsive to receiving the user response, determine a severity level of the user response, wherein the severity level includes a low severity level, medium severity level, and high severity level; and
implement automated procedures at the check-in application based on the determined severity level of the user response, in which the automated procedures includes rendering a second screen that addresses and is unique to the user's severity level, wherein:
a determination of the low or medium severity levels for the user causes the user computing device to render a follow-up screen for the user to provide additional personal information, and
based on the additional personal information provided by the user, render a final screen that concludes the check-in and also provides the user with an opportunity to initiate the check-in process; and
a determination of the high severity level for the user causes the user computing device to,
display a countdown timer leading up to the check-in application connecting to a medical provider operating a remote device,
automatically initiate a connection with the medical provider operating the remote device, or
render a screen indicating that medical providers are unavailable and providing alternative options for the user to get help; and
an administrative computing device configured with backend access to the check-in application's system, comprising:
storing at least the user response and a history of user responses;
rendering at least the user response and the history of user responses and mental health information; and
rendering evaluation and follow-up information for administration on a per-patient basis which is at least in part affected by the user response.

2. The system of claim 1, wherein the check-in application renders a number of patients awaiting evaluation and follow-ups, in which multiple follow-up columns are rendered which focus on differing temporal parameters.

3. The system of claim 1, further comprising:
rendering, at the administrative computing device, potential earnings for the administration, in which the potential earnings are rendered on a same screen as the evaluation and follow-up information.

4. The system of claim 1, further comprising:
rendering, at the administrative computing device, treatment information for multiple patients, in which the treatment information includes at least therapy and coaching in distinct columns.

5. The system of claim 4, wherein the treatment information further includes coaching in a distinct column.

6. The system of claim 1, further comprising:
receiving, at the administrative computing device, user input that selects a patient; and
responsive to receiving the user input, rendering, at the administrative computing device, information specific to that patient, in which the information includes diagrams representing historical user check-in responses and administration notes about the patient.

7. A method for rendering a graphical user interface (GUI) that enables a user to input updates to their mental health status, comprising:
logging, at a user computing device, in to a unique user's account associated with the check-in application responsive to receiving login credentials from a user;
rendering, at a user computing device, a first screen of the GUI which includes an inquiry regarding the user's mental health status to initiate a check-in process;
receiving, at a user computing device, a user response to the presented inquiry, in which the user response indicates a current status of the user's mental health;
responsive to receiving the user response, determining, at a user computing device, a severity level of the user response, wherein the severity level includes a low severity level, medium severity level, and high severity level; and
implementing, at a user computing device, automated procedures at the check-in application based on the determined severity level of the user response, in which the automated procedures includes rendering a second screen that addresses and is unique to the user's severity level, wherein:
a determination of the low or medium severity levels for the user causes the user computing device to render a follow-up screen for the user to provide additional personal information, and
based on the additional personal information provided by the user, render a final screen that concludes the check-in and also provides the user with an opportunity to initiate the check-in process; and
a determination of the high severity level for the user causes the user computing device to:
display a countdown timer leading up to the check-in application connecting to a medical provider operating a remote device,
automatically initiate a connection with the medical provider operating the remote device, or
render a screen indicating that medical providers are unavailable and providing alternative options for the user to get help;
storing, at an administrative computing device, at least the user response and a history of user responses;
rendering, at an administrative computing device, at least the user response and the history of user responses and mental health information; and
rendering, at an administrative computing device, evaluation and follow-up information for administration on a per-patient basis which is at least in part affected by the user response.

8. The method of claim 7, wherein the check-in application renders a number of patients awaiting evaluation and follow-ups, in which multiple follow-up columns are rendered which focus on differing temporal parameters.

9. The method of claim 7, further comprising:
rendering, at the administrative computing device, potential earnings for the administration, in which the potential earnings are rendered on a same screen as the evaluation and follow-up information.

10. The method of claim 7, further comprising:
rendering, at the administrative computing device, treatment information for multiple patients, in which the treatment information includes at least therapy and coaching in distinct columns.

11. The method of claim 10, wherein the treatment information further includes coaching in a distinct column.

12. The method of claim 7, further comprising:
receiving, at the administrative computing device, user input that selects a patient; and
responsive to receiving the user input, rendering, at the administrative computing device, information specific to that patient, in which the information includes diagrams representing historical user check-in responses and administration notes about the patient.

13. One or more hardware-based non-transitory computer-readable memory devices disposed in one or more computing devices, the computer-readable instructions, when executed by one or more processors, cause the one or more computing devices to:
log in to a unique user's account associated with the check-in application responsive to receiving login credentials from a user;
render a first screen of the GUI which includes an inquiry regarding the user's mental health status to initiate a check-in process;
receive a user response to the presented inquiry, in which the user response indicates a current status of the user's mental health;
responsive to receiving the user response, determine a severity level of the user response, wherein the severity level includes a low severity level, medium severity level, and high severity level; and
implement automated procedures at the check-in application based on the determined severity level of the user response, in which the automated procedures includes rendering a second screen that addresses and is unique to the user's severity level, wherein;
a determination of the low or medium severity levels for the user causes the user computing device to render a follow-up screen for the user to provide additional personal information, and
based on the additional personal information provided by the user, render a final screen that concludes the check-in and also provides the user with an opportunity to initiate the check-in process, and
a determination of the high severity level for the user causes the user computing device to;
display a countdown timer leading up to the check-in application connecting to a medical provider operating a remote device,
automatically initiate a connection with the medical provider operating the remote device, or
render a screen indicating that medical providers are unavailable and providing alternative options for the user to get help;
store at least the user response and a history of user responses;
render at least the user response and the history of user responses and mental health information; and
render evaluation and follow-up information for administration on a per-patient basis which is at least in part affected by the user response.

14. The one or more hardware-based non-transitory computer-readable memory devices of claim 13, wherein the check-in application renders a number of patients awaiting evaluation and follow-ups, in which multiple follow-up columns are rendered which focus on differing temporal parameters.

15. The one or more hardware-based non-transitory computer-readable memory devices of claim 13, wherein the executed instructions further cause the one or more computing devices to:
render potential earnings for the administration, in which the potential earnings are rendered on a same screen as the evaluation and follow-up information.

16. The one or more hardware-based non-transitory computer-readable memory devices of claim 13, further comprising:
rendering, at the administrative computing device, treatment information for multiple patients, in which the treatment information includes at least therapy and coaching in distinct columns.

17. The one or more hardware-based non-transitory computer-readable memory devices of claim 16, wherein the treatment information further includes coaching in a distinct column.

* * * * *